US007819801B2

(12) United States Patent
Miles et al.

(10) Patent No.: US 7,819,801 B2
(45) Date of Patent: Oct. 26, 2010

(54) SURGICAL ACCESS SYSTEM AND RELATED METHODS

(75) Inventors: Patrick Miles, San Diego, CA (US);
Scot Martinelli, Poway, CA (US); Eric Finley, Lancaster, CA (US); James Gharib, San Diego, CA (US); Allen Farquhar, San Diego, CA (US);
Norbert Kaula, Arvada, CO (US);
Jeffrey Blewett, San Diego, CA (US);
Goretti Medeiros, legal representative, Plantsville, CT (US)

(73) Assignee: Nuvasive, Inc., San Diego, CA (US)

( * ) Notice: Subject to any disclaimer, the term of this patent is extended or adjusted under 35 U.S.C. 154(b) by 1659 days.

(21) Appl. No.: 10/789,797

(22) Filed: Feb. 27, 2004

(65) Prior Publication Data

US 2009/0124860 A1    May 14, 2009

Related U.S. Application Data

(60) Provisional application No. 60/450,806, filed on Feb. 27, 2003.

(51) Int. Cl.
*A61B 1/32* (2006.01)

(52) U.S. Cl. ................ 600/224; 600/202; 600/210; 600/214; 600/219

(58) Field of Classification Search ......... 607/129–131, 607/117, 119, 374; 606/129, 108, 40, 99; 600/202, 210, 212, 214, 215, 219, 221–224
See application file for complete search history.

(56) References Cited

U.S. PATENT DOCUMENTS

| 208,227 A | 9/1878 | Dorr |
| 972,983 A | 10/1910 | Arthur |
| 1,328,624 A | 1/1920 | Graham |
| 1,548,184 A | 8/1925 | Cameron |
| 2,704,064 A | 3/1955 | Fizzell et al. ............. 128/2.1 |
| 2,736,002 A | 2/1956 | Oriel |
| 2,808,826 A | 10/1957 | Reiner et al. |
| 3,364,929 A | 1/1968 | Ide et al. ............. 128/172.1 |
| 3,664,329 A | 5/1972 | Naylor ............. 128/2.1 R |

(Continued)

FOREIGN PATENT DOCUMENTS

DE            299 08 259            7/1999

(Continued)

OTHER PUBLICATIONS

"Electromyography System", *International Search Report*, International Application No. PCT/US00/32329,(Apr. 27, 2001),9 pages.

(Continued)

*Primary Examiner*—Eduardo C Robert
*Assistant Examiner*—Ellen C. Hammond
(74) *Attorney, Agent, or Firm*—Jonathan Spangler; Rory Schermerhorn

(57) ABSTRACT

A surgical access system including a tissue distraction assembly and a tissue retraction assembly, both of which may be equipped with one or more electrodes for use in detecting the existence of (and optionally the distance and/or direction to) neural structures before, during, and after the establishment of an operative corridor to a surgical target site.

57 Claims, 23 Drawing Sheets

U.S. PATENT DOCUMENTS

| | | | | |
|---|---|---|---|---|
| 3,682,162 A | 8/1972 | Colyer | | 128/2.1 R |
| 3,785,368 A | 1/1974 | McCarthy et al. | | 128/2.1 Z |
| 3,830,226 A | 8/1974 | Staub et al. | | 128/2.1 R |
| 3,957,036 A | 5/1976 | Normann | | 128/2.1 R |
| 4,099,519 A | 7/1978 | Warren | | 128/2.1 R |
| 4,164,214 A | 8/1979 | Stark et al. | | |
| 4,207,897 A | 6/1980 | Lloyd et al. | | 128/303.1 |
| 4,224,949 A | 9/1980 | Scott et al. | | 128/734 |
| 4,226,228 A | 10/1980 | Shin et al. | | |
| 4,235,242 A | 11/1980 | Howson et al. | | 128/695 |
| 4,285,347 A | 8/1981 | Hess | | 128/785 |
| 4,291,705 A | 9/1981 | Severinghaus et al. | | 600/546 |
| 4,461,300 A | 7/1984 | Christensen | | |
| 4,515,168 A | 5/1985 | Chester et al. | | 128/741 |
| 4,519,403 A | 5/1985 | Dickhudt | | 128/785 |
| 4,545,374 A | 10/1985 | Jacobson | | |
| 4,561,445 A | 12/1985 | Berke et al. | | 128/642 |
| 4,562,832 A | 1/1986 | Wilder et al. | | |
| 4,573,448 A | 3/1986 | Kambin | | |
| 4,592,369 A | 6/1986 | Davis et al. | | 128/733 |
| 4,595,018 A | 6/1986 | Rantala | | 128/733 |
| 4,611,597 A | 9/1986 | Kraus | | |
| 4,633,889 A | 1/1987 | Talalla | | 128/784 |
| 4,658,835 A | 4/1987 | Pohndorf | | 128/785 |
| 4,744,371 A | 5/1988 | Harris | | 607/117 |
| 4,759,377 A | 7/1988 | Dykstra | | 128/733 |
| 4,784,150 A | 11/1988 | Voorhies et al. | | |
| 4,807,642 A | 2/1989 | Brown | | 128/733 |
| 4,892,105 A | 1/1990 | Prass | | 128/741 |
| 4,913,134 A | 4/1990 | Luque | | |
| 4,926,865 A | 5/1990 | Oman | | 128/421 |
| 4,962,766 A | 10/1990 | Herzon | | 128/741 |
| 4,964,411 A | 10/1990 | Johnson et al. | | 128/733 |
| 5,007,902 A | 4/1991 | Witt | | 604/117 |
| 5,058,602 A | 10/1991 | Brody | | 128/733 |
| 5,081,990 A | 1/1992 | Deletis | | 128/642 |
| 5,092,344 A | 3/1992 | Lee | | 128/741 |
| 5,127,403 A | 7/1992 | Brownlee | | 128/419 P |
| 5,161,533 A | 11/1992 | Prass et al. | | 128/639 |
| 5,171,279 A | 12/1992 | Mathews | | |
| 5,196,015 A | 3/1993 | Neubardt | | 606/61 |
| RE34,390 E | 9/1993 | Culver | | 128/731 |
| 5,255,691 A | 10/1993 | Otten | | 607/117 |
| 5,282,468 A | 2/1994 | Klepinski | | 128/642 |
| 5,284,153 A * | 2/1994 | Raymond et al. | | 600/554 |
| 5,284,154 A | 2/1994 | Raymond et al. | | 128/741 |
| 5,299,563 A | 4/1994 | Seton | | |
| 5,312,417 A | 5/1994 | Wilk | | 606/114 |
| 5,313,956 A | 5/1994 | Knutsson et al. | | 128/741 |
| 5,327,902 A | 7/1994 | Lemmen | | 128/734 |
| 5,333,618 A | 8/1994 | Lekhtman et al. | | 128/734 |
| 5,375,067 A | 12/1994 | Berchin | | 364/487 |
| 5,383,876 A | 1/1995 | Nardella | | 606/49 |
| 5,450,845 A | 9/1995 | Axelgaard | | |
| 5,474,057 A * | 12/1995 | Makower et al. | | 600/214 |
| 5,474,558 A | 12/1995 | Neubardt | | 606/79 |
| 5,480,440 A | 1/1996 | Kambin | | |
| 5,482,038 A | 1/1996 | Ruff | | 128/642 |
| 5,484,437 A | 1/1996 | Michelson | | |
| 5,509,893 A | 4/1996 | Pracas | | |
| 5,540,235 A | 7/1996 | Wilson | | 128/741 |
| 5,549,656 A | 8/1996 | Reiss | | 607/48 |
| 5,560,372 A | 10/1996 | Cory | | 128/741 |
| 5,566,678 A | 10/1996 | Cadwell | | 128/731 |
| 5,571,149 A | 11/1996 | Liss et al. | | |
| 5,579,781 A | 12/1996 | Cooke | | 128/733 |
| 5,593,429 A | 1/1997 | Ruff | | 607/116 |
| 5,599,279 A | 2/1997 | Slotman et al. | | |
| 5,630,813 A | 5/1997 | Kieturakis | | 606/46 |
| 5,667,508 A | 9/1997 | Errico et al. | | |
| 5,671,752 A | 9/1997 | Sinderby et al. | | 128/733 |
| 5,681,265 A * | 10/1997 | Maeda et al. | | 600/219 |
| 5,707,359 A | 1/1998 | Bufalini | | 604/104 |
| 5,711,307 A | 1/1998 | Smits | | 128/733 |
| 5,728,046 A | 3/1998 | Mayer et al. | | |
| 5,741,253 A | 4/1998 | Michelson | | |
| 5,759,159 A | 6/1998 | Masreliez | | |
| 5,772,661 A * | 6/1998 | Michelson | | 606/86 A |
| 5,775,331 A * | 7/1998 | Raymond et al. | | 600/554 |
| 5,776,144 A | 7/1998 | Leysieffer et al. | | |
| 5,779,642 A | 7/1998 | Nightengale | | 600/461 |
| 5,785,658 A | 7/1998 | Benaron | | |
| 5,792,044 A | 8/1998 | Foley et al. | | |
| 5,797,854 A | 8/1998 | Hedgecock | | 600/554 |
| 5,814,073 A | 9/1998 | Bonutti | | 606/232 |
| 5,830,151 A | 11/1998 | Hadzic et al. | | 600/554 |
| 5,851,191 A | 12/1998 | Gozani | | 600/554 |
| 5,853,373 A | 12/1998 | Griffith et al. | | 600/554 |
| 5,860,973 A | 1/1999 | Michelson | | |
| 5,862,314 A | 1/1999 | Jeddeloh | | |
| 5,872,314 A | 2/1999 | Clinton | | |
| 5,885,210 A * | 3/1999 | Cox | | 600/214 |
| 5,885,219 A | 3/1999 | Nightengale | | 600/461 |
| 5,888,196 A | 3/1999 | Bonutti | | 600/204 |
| 5,902,231 A | 5/1999 | Foley et al. | | |
| 5,928,139 A | 7/1999 | Koros | | |
| 5,928,158 A | 7/1999 | Aristides | | 600/547 |
| 5,935,131 A | 8/1999 | Bonutti et al. | | |
| 5,938,688 A | 8/1999 | Schiff | | |
| 5,944,658 A | 8/1999 | Koros et al. | | |
| 5,976,094 A | 11/1999 | Gozani et al. | | 600/483 |
| 6,004,262 A | 12/1999 | Putz et al. | | 600/114 |
| 6,024,696 A * | 2/2000 | Hoftman et al. | | 600/224 |
| 6,027,456 A | 2/2000 | Feler et al. | | 600/554 |
| 6,038,469 A | 3/2000 | Karlsson et al. | | |
| 6,038,477 A | 3/2000 | Kayyali | | 607/72 |
| 6,050,992 A | 4/2000 | Nichols | | 606/41 |
| 6,074,343 A | 6/2000 | Nathanson et al. | | |
| 6,095,987 A | 8/2000 | Shmulewitz | | |
| 6,104,957 A | 8/2000 | Alo et al. | | 607/46 |
| 6,104,960 A | 8/2000 | Duysens et al. | | |
| 6,120,503 A | 9/2000 | Michelson | | |
| 6,126,660 A * | 10/2000 | Dietz | | 606/61 |
| 6,132,386 A | 10/2000 | Gozani et al. | | 600/554 |
| 6,132,387 A | 10/2000 | Gozani et al. | | 600/554 |
| 6,135,965 A | 10/2000 | Tumer et al. | | 600/476 |
| 6,139,493 A | 10/2000 | Koros et al. | | |
| 6,146,335 A | 11/2000 | Gozani | | 600/554 |
| 6,152,871 A | 11/2000 | Foley et al. | | |
| 6,161,047 A | 12/2000 | King et al. | | 607/62 |
| 6,181,961 B1 | 1/2001 | Prass | | |
| 6,196,969 B1 * | 3/2001 | Bester et al. | | 600/224 |
| 6,206,826 B1 * | 3/2001 | Mathews et al. | | 600/210 |
| 6,224,549 B1 | 5/2001 | Drongelen | | 600/300 |
| 6,259,945 B1 | 7/2001 | Epstein et al. | | 600/547 |
| 6,264,651 B1 * | 7/2001 | Underwood et al. | | 606/32 |
| 6,266,558 B1 | 7/2001 | Gozani et al. | | 600/547 |
| 6,273,905 B1 | 8/2001 | Streeter | | |
| 6,292,701 B1 | 9/2001 | Prass et al. | | 607/116 |
| 6,306,100 B1 | 10/2001 | Prass | | |
| 6,312,392 B1 | 11/2001 | Herzon | | 600/554 |
| 6,325,764 B1 | 12/2001 | Griffith et al. | | |
| 6,334,068 B1 | 12/2001 | Hacker | | |
| 6,360,750 B1 * | 3/2002 | Gerber et al. | | 128/898 |
| 6,425,859 B1 | 7/2002 | Foley et al. | | |
| 6,425,901 B1 | 7/2002 | Zhu et al. | | |
| 6,450,952 B1 * | 9/2002 | Rioux et al. | | 600/223 |
| 6,451,015 B1 | 9/2002 | Rittman, III et al. | | |
| 6,466,817 B1 * | 10/2002 | Kaula et al. | | 600/546 |
| 6,468,205 B1 | 10/2002 | Mollenauer et al. | | |
| 6,468,207 B1 | 10/2002 | Fowler, Jr. | | |
| 6,500,128 B2 * | 12/2002 | Marino | | 600/554 |
| 6,524,320 B2 | 2/2003 | DiPoto | | |
| 6,535,759 B1 | 3/2003 | Epstein et al. | | |

| | | | |
|---|---|---|---|
| 6,564,078 B1 * | 5/2003 | Marino et al. | 600/373 |
| 6,579,244 B2 | 6/2003 | Goodwin | |
| 6,620,157 B1 * | 9/2003 | Dabney et al. | 606/34 |
| 6,719,692 B2 | 4/2004 | Kleffner et al. | |
| 6,760,616 B2 | 7/2004 | Hoey et al. | |
| 6,796,985 B2 | 9/2004 | Bolger et al. | |
| 6,810,281 B2 | 10/2004 | Brock et al. | |
| 6,819,956 B2 | 11/2004 | DiLorenzo | |
| 6,847,849 B2 | 1/2005 | Mamo et al. | |
| 6,849,047 B2 | 2/2005 | Goodwin | |
| 6,855,105 B2 | 2/2005 | Jackson, III et al. | |
| 6,902,569 B2 | 6/2005 | Parmer et al. | |
| 6,926,728 B2 | 8/2005 | Zucherman et al. | |
| 6,929,606 B2 | 8/2005 | Ritland | |
| 6,945,933 B2 | 9/2005 | Branch | |
| 6,951,538 B2 * | 10/2005 | Ritland | 600/210 |
| 7,047,082 B1 | 5/2006 | Schrom et al. | |
| 7,050,848 B2 | 5/2006 | Hoey et al. | |
| 7,079,883 B2 | 7/2006 | Marino et al. | |
| 7,089,059 B1 | 8/2006 | Pless | |
| 7,177,677 B2 * | 2/2007 | Kaula et al. | 600/546 |
| 7,207,949 B2 * | 4/2007 | Miles et al. | 600/554 |
| 7,261,688 B2 | 8/2007 | Smith et al. | |
| 7,470,236 B1 * | 12/2008 | Kelleher et al. | 600/554 |
| 7,473,222 B2 * | 1/2009 | Dewey et al. | 600/210 |
| 7,481,766 B2 * | 1/2009 | Lee et al. | 600/214 |
| 7,582,058 B1 | 9/2009 | Miles et al. | |
| 7,643,884 B2 * | 1/2010 | Pond et al. | 607/116 |
| 2001/0039949 A1 | 11/2001 | Loubser | |
| 2001/0056280 A1 | 12/2001 | Underwood et al. | |
| 2002/0007129 A1 | 1/2002 | Marino | 600/546 |
| 2002/0010392 A1 * | 1/2002 | Desai | 600/374 |
| 2002/0072686 A1 | 6/2002 | Hoey et al. | 600/547 |
| 2002/0123780 A1 | 9/2002 | Grill et al. | |
| 2002/0161415 A1 | 10/2002 | Cohen et al. | |
| 2002/0193843 A1 | 12/2002 | Hill et al. | |
| 2003/0032966 A1 | 2/2003 | Foley et al. | |
| 2003/0105503 A1 | 6/2003 | Marino | |
| 2003/0149341 A1 | 8/2003 | Clifton | |
| 2003/0225405 A1 * | 12/2003 | Weiner | 606/54 |
| 2004/0199084 A1 | 10/2004 | Kelleher et al. | |
| 2004/0225228 A1 | 11/2004 | Ferree | |
| 2005/0004593 A1 | 1/2005 | Simonson | |
| 2005/0004623 A1 | 1/2005 | Miles et al. | |
| 2005/0033380 A1 | 2/2005 | Tanner et al. | |
| 2005/0075578 A1 | 4/2005 | Gharib et al. | |
| 2005/0080320 A1 * | 4/2005 | Lee et al. | 600/214 |
| 2005/0149035 A1 | 7/2005 | Pimenta et al. | |
| 2005/0182454 A1 | 8/2005 | Gharib et al. | |
| 2005/0192575 A1 | 9/2005 | Pacheco | |
| 2006/0025703 A1 | 2/2006 | Miles et al. | |
| 2006/0052828 A1 | 3/2006 | Kim et al. | |
| 2006/0069315 A1 | 3/2006 | Miles et al. | |
| 2006/0224078 A1 | 10/2006 | Hoey et al. | |
| 2007/0016097 A1 | 1/2007 | Farquhar et al. | |
| 2007/0198062 A1 | 8/2007 | Miles et al. | |
| 2007/0293782 A1 | 12/2007 | Marino | |
| 2008/0058606 A1 | 3/2008 | Miles et al. | |
| 2008/0064976 A1 | 3/2008 | Kelleher et al. | |
| 2008/0064977 A1 | 3/2008 | Kelleher et al. | |
| 2008/0065178 A1 | 3/2008 | Kelleher et al. | |
| 2008/0071191 A1 | 3/2008 | Kelleher et al. | |
| 2008/0097164 A1 | 4/2008 | Miles et al. | |
| 2009/0124860 A1 | 5/2009 | Miles et al. | |
| 2009/0138050 A1 | 5/2009 | Ferree | |
| 2009/0192403 A1 | 7/2009 | Gharib et al. | |
| 2009/0204016 A1 | 8/2009 | Gharib et al. | |

FOREIGN PATENT DOCUMENTS

| | | |
|---|---|---|
| EP | 0972538 A2 | 1/2000 |
| FR | 2 795 624 | 1/2001 |
| WO | WO-0038574 A1 | 7/2000 |
| WO | WO 00/67645 | 11/2000 |
| WO | WO-0066217 A1 | 11/2000 |
| WO | WO-0137728 A1 | 5/2001 |
| WO | WO 02/054960 | 7/2002 |
| WO | WO 03/005887 | 1/2003 |
| WO | WO 03/026482 | 4/2003 |
| WO | WO-03037170 A3 | 5/2003 |
| WO | WO-2005013805 A3 | 2/2005 |
| WO | WO 2005/030318 | 4/2005 |
| WO | WO 2006/042241 | 4/2006 |
| WO | WO 2006/066217 | 6/2006 |

OTHER PUBLICATIONS

"Nerve Proximity and Status Detection System and Method", *International Search Report*, International Application No. PCT/US01/18606,(Oct. 18, 2001),6 pages.

"Relative Nerve Movement and Status Detection System and Method", *International Search Report*, International Application No. PCT/US01/18579,(Jan. 15, 2002),6 pages.

"System and Method for Determining Nerve Proximity, Direction, and Pathology During Surgery", *International Search Report*, International Application No. PCT/US02/22247,(Mar. 27, 2003),4 pages.

"System and Methods for Determining Nerve Direction to a Surgical Instrument", *International Search Report*, International Application No. PCT/US03/02056,(Aug. 12, 2003),5 pages.

"Systems and Methods for Performing Percutaneous Pedicle Integrity Assessments", *International Search Report*, International Application No. PCT/US02/35047,(Aug. 11, 2003),5 pages.

"Systems and Methods for Performing Surgery Procedures and Assessments", *International Search Report*, International Application No. PCT/US02/30617,(Jun. 5, 2003),4 pages.

Bose, et al., "Neurophysiologic Monitoring of Spinal Nerve Root Function During Instrumented Posterior Lumbar Spine Surgery", *Spine*, 27(13), (2002),1444-1450.

Calancie, et al., "Stimulus-Evoked EMG Monitoring During Transpedicular Lumbosacral Spine Instrumentation", *Spine*, 19(24), (1994),2780-2786.

Clements, et al., "Evoked and Spontaneous Electromyography to Evaluate Lumbosacral Pedicle Screw Placement", *Spine*, 21(5), (1996),600-604.

Ford, et al., "Electrical Characteristics of Peripheral Nerve Stimulators Implications for Nerve Localization", *Regional Anesthesia*, 9, (1984),73-77.

Glassman, et al., "A Prospective Analysis of Intraoperative Electromyographic Monitoring of Pedicle Screw Placement With Computed Tomographic Scan Confirmation", *Spine* , 20(12), (1995),1375-1379.

Greenblatt, et al., "Needle Nerve Stimulator-Locator: Nerve Blocks with a New Instrument for Locating Nerves", *Anesthesia & Analgesia*, 41(5), (1962),599-602.

Holland, N. , "Intraoperative Electromyography During Thoracolumbar Spinal Surgery", *Spine*, 23(17), (1998),1915-1922.

Lenke, et al., "Triggered Electromyographic Threshold for Accuracy of Pedicle Screw Placement", *Spine*, 20 (14), (1995),1585-1591.

Maguire, et al., "Evaluation of Intrapedicular Screw Position Using Intraoperative Evoked Electromyography", *Spine*, 20(9), (1995),1068-1074.

Martin, et al., "Initiation of Erection and Semen Release by Rectal Probe Electrostimulation (RPE)", *The Williams & Wilkins Co.*, (1983),637-642.

Pither, et al., ""The Use of Peripheral Nerve Stimulators for Regional Anesthesia: Review of Experimental Characteristics, Technique, and Clinical Applications"", *Regional Anesthesia*, (1985),10:47-53.

Raj, et al., "Infraclavicular Brachial Plexus Block—A New Approach", *Anesthesia and Analgesia*, (52)6, (1973),897-904.

Raj, et al., "The Use of Peripheral Nerve Stimulators For Regional Anesthesia", *Clinical Issues In Regional Anesthesia*, 1 (4), (1985),1-6.

Raj, et al., "Use of The nerve Stimulator of Peripheral Blocks", *Regional Anesthesia*, (Apr.-Jun. 1980),14-21.

Raymond, et al., "The Nerve Seeker: A System for Automated Nerve Localization", *Regional Anesthesia*, 17(3), (1992),151-162.

Shafik, "Cavernous Nerve Simulation through an Extrapelvic Subpubic Approach: Role in Pencil Erection", *Eur. Urol*, 26, (1994),98-102.

Toleikis, et al., "The Usefulness of Electrical Stimulation for Assessing Pedicle Screw Replacements", *Journal of Spinal Disorder*, 13(4), (2000),283-289.

"Brackmann II EMG System", *Medical Electronics*, (1999),4 pages.

"Neurovision SE Nerve Locator/Monitor", *RLN Systems, Inc. Operators Manual*, (1999),22 pages.

"The Brackmann II EMG Monitoring System", *Medical Electronics Co. Operator's Manual Version 1.1*, (1995),50 pages.

"The Nicolet Viking IV", *Nicolet Biomedical Products*, (1999),6 pages.

Anderson, D. G., et al., "Pedicle screws with high electrical resistance: a potential source of error with stimulus-evoked EMG", *Spine*, 27(14):, Department of Orthopaedic Surgery, University of Virginia,(Jul. 15, 2002),1577-1581.

Danesh-Clough, T. , et al., "The use of evoked EMG in detecting misplaced thoracolumbar pedicle screws", *Spine*, 26(12), Orthopaedic Department, Dunedin Hospital,(Jun. 15, 2001),1313-1316.

Darden, B. V., et al., "A comparison of impedance and electromyogram measurments in detecting the presence of pedicle wall breakthrough", *Spine*. 23(2), Charlotte Spine Center, North Carolina,(Jan. 15, 1998),256-262.

Ebraheim, N. A., et al., "Anatomic relations between the lumbar pedicle and the adjacent neural structures", *Spine*. 22(20), Department of Orthopaedic Surgery, Medical College of Ohio,(Oct. 15, 1997),2338-2341.

Haig, "Point of view", *Spine* 27 (24), 2819.

Haig, A. J., et al., "The relation among spinal geometry on MRI, paraspinal electromyographic abnormalities, and age in persons referred for electrodiagnostic testing of low back symptoms", *Spine*. 27(17), Department of Physical Medicine and Rehabilitation, University of Michigan,(Sep. 1, 2002),1918-1925.

Holland, N. R., et al., "Higher electrical stimulus intensities are required to activate chronically compressed nerve roots. Implications for intraoperative electromyographic pedicle screw testing", *Spine*. 23(2), Department of Neurology, Johns Hopkins University School of Medicine,(Jan. 15, 1998),224-227.

Minahan, R. E., et al., "The effect of neuromuscular blockade on pedicle screw stimulation thresholds", *Spine*. 25(19), Department of Neurology, Johns Hopkins University, School of Medicine,(Oct. 1, 2000),2526-2530.

Journee, H. L., et al., "System for Intra-Operative Monitoring of the Cortical Integrity of the Pedicle During Screw Placement in Low-Back Surgery: Design and Clinical Results", *Sensory and neuromuscular diagnostic instrumentation and data analysis, 18th Annual International Conference on Engineering in Medicine and Biology Society*, 1(31), (Oct. 1996),144-145.

Anatomy of the Lumbar Spine in MED TM MicroEndoscopic Discectomy (1997 Ludann Grand Rapids MI), 14 pgs.

Dirksmeier et al., "Microendoscopic and Open Laminotomy and Discectomy in Lumbar Disc Disease" *Seminars in Spine Surgery*, 1999, 11(2): 138-146.

METRx Delivered Order Form, 1999, 13 pages.

Medtronic Sofamor Danek "METRx™ MicroDisectomy System," *Medtronic Sofamor Danek USA*, 2000, 21 pgs.

Medtronic Sofamor Danek "METRx System Surgical Technique," 2004, 22 pages.

"MetRx System MicroEndoscopic Discectomy: An Evolution in Minimally Invasive Spine Surgery," *Sofamor Danek*, 1999, 6 pages.

Smith and Foley "MetRx System MicroEndoscopic Discectomy: Surgical Technique" *Medtronic Sofamor Danek*, 2000, 24 pages.

"Sofamor Danek MED Microendoscopic Discectomy System Brochure" including Rapp "New endoscopic lumbar technique improves access preserves tissue" Reprinted with permission from: *Orthopedics Today*, 1998, 18(1): 2 pages.

Japanese Patent Office JP Patent Application No. 2006-528306 Office Action with English Translation, Jun. 10, 2009, 4 pages.

Plaintiffs' Preliminary Invalidity Contentions re US Patents 7207949; 7470236 and 7582058, Sep. 18, 2009, 19 pages.

Plaintiffs' Preliminary Invalidity Contentions-Appendices, Sep. 18, 2009, 191 pages.

Plaintiffs' Supplemental Preliminary Invalidity Contentions re US Patents 7207949, 7470236, and 7582058, Sep. 29, 2009, 21 pages.

Plaintiffs' Supplemental Preliminary Invalidity Contentions-Appendices, Sep. 29, 2009, 294 pages.

Axon 501(k) Notification: Epoch 2000 Neurological Workstation, Dec. 3, 1997, 464 pages.

Foley and Smith, "Microendoscopic Discectomy," *Techniques in Neurosurgery*, 1997, 3(4):301-307.

Medtronic Sofamor Danek "UNION™ / UNION-L™ Anterior & Lateral Impacted Fusion Devices: Clear choice of stabilization," *Medtronic Sofamor Danek*, 2000, 4 pages.

NuVasive Vector™ Cannulae, 1 page (prior to Sep. 25, 2003).

NuVasive Triad™ Tri-Columnar Spinal EndoArthrodesis™ via Minimally Invasive Guidance, 1 page (prior to Sep. 25, 2003).

NuVasive Triad™ Cortical Bone Allograft, 1 page (prior to Sep. 25, 2003).

NuVasive Vertebral Body Access System, 1 page (prior to Sep. 25, 2003).

Marina, "New Technology for Guided Navigation with Real Time Nerve Surveillance for Minimally Invasive Spine Discectomy & Arthrodesis," *Spineline*, 2000, p. 39.

NuVasive "INS-1 Screw Test," 2001, 10 pages.

NuVasive letter re 510k Neuro Vision JJB System, Oct. 16, 2001, 5 pages.

NuVasive letter re 510k Guided Arthroscopy System, Oct. 5, 1999, 6 pages.

NuVasive letter re 510k INS-1 Intraoperative Nerve Surveillance System, Nov. 13, 2000, 7 pages.

"NuVasiveTM Receives Clearance to Market Two Key Elem Minimally Invasive Spine Surgery System," Nov. 27, 2001, 20 pages.

Schick et al., "Microendoscopic lumbar discectomy versus open surgery: an intraoperative EMG study," *Eur Spine J*, 2002, 11: 20-26.

NuVasive letter re: 510(k) for Neurovision JJB System (Summary), Sep. 25, 2001, 28 pages.

NuVasive letter re: Special 510(k) Premarket Notification: Neurovision JJB System (Device Description), Jul. 3, 2003, 18 pages.

NuVasive letter re: Special 510(k) Premarket Notification: Neurovision JJB System (Device Description), Mar. 1, 2004, 16 pages.

NuVasive letter re: Special 510(k) Premarket Notification: Neurovision JJB System (Device Description), May 26, 2005, 17 pages.

NuVasive letter re: 510(k) Premarket Notification: Neurovision JJB System (Device Description), Jun. 24, 2005, 16 pages.

NuVasive letter re: Special 510(k) Premarket Notification: Neurovision JJB System (Device Description), Sep. 14, 2006, 17 pages.

NuVasive 510(k) Premarket Notification: Neurovision JJB System (Device Description), Aug. 20, 2007, 8 pages.

NuVasive letter re: 510(k) Premarket Notification: Guided Spinal Arthroscopy System (Device Description), Feb. 1, 1999, 40 pages.

NuVasive 510(k) Premarket Notification: Spinal System (Summary), Apr. 12, 2004, 10 pages.

NuVasive 510(k) Summary NIM Monitor, Sep. 4, 1998, 4 pages.

NuVasive correspondence re 510(k) Premarket Notification INS-1 Intraoperative Nerve Surveillance System: Section IV Device Description, pp. 12-51 (prior to Sep. 25, 2003).

NuVasive letter re 510(k) Premarket Notification INS-1 Intraoperative Nerve Surveillance System, Aug. 24, 2000, 81 pages.

Isley et al., "Recent Advances in Intraoperative Neuromonitoring of Spinal Cord Function: Pedicle Screw Stimulation Techniques," *American Journal of Electroneurodagnostic Technology*, Jun. 1997, 37(2): 93-126.

Mathews et al., "Laparoscopic Discectomy with Anterior Lumbar Interbody Fusion," *Spine*, 1995, 20(16): 1797-1802.

Rose et al., "Persistently Electrified Pedicle Stimulation Instruments in Spinal Instrumentation: Techniques and Protocol Development," *Spine*, 1997, 22(3): 334-343.

Journee et al., "System for Intra-Operative Monitoring of the Cortical Integrity of the Pedicle During Pedicle Screw Placement in Low-Back Surgery: Design and Clinical Resuslts," *Sensory and Neuromuscular Diagnostic Instrumentation and Data Analysis I, 18th Annual International Conference on Engineering in Medicine and Biology Society*, Amsterdam, 1996, pp. 144-145.

Medtronic Sofamor Danek "UNION™ / UNION-L™ Anterior & Lateral Impacted Fusion Devices: Surgical Technique" *Medtronic Sofamor Danek*, 2001, 20 pages.

Defendant's Disclosure of Asserted Claims and Preliminary Infringement Contentions Regarding USP 7207949; 7470236 and 7582058, Aug. 31, 2009, 21 pages.

Bergey et al., "Endoscopic Lateral Transpsoas Approach to the Lumbar Spine," *Spine*, 2004, 29(15): 1681-1688.

Dezawa et al., "Retroperitoneal Laparoscopic Lateral Approach to the Lumbar Spine: A New Approach, Technique, and Clinical Trial," *Journal of Spinal Disorders*, 2000, 13(2): 138-143.

Gardocki, "Tubular diskectomy minimizes collateral damage: A logical progression moves spine surgery forward," *AAOS Now*, 2009, 5 pages.

Hovorka et al., "Five years' experience of retroperitoneal lumbar and thoracolumbar surgery," *Eur. Spine J.*, 2000, 9(1): S30-S34.

Kossman et al., "The use of a retractor system (SynFrame) for open, minimal invasive reconstruction of the anterior column of the thoracic and lumbar spine," *Eur Spine J.*, 2001, 10: 396-402.

Mayer, "A New Microsurgical Technique for Minimally Invasive Anterior Lumbar Interbody Fusion," *Spine*, 1997, 22(6): 691-699.

Mayer, "The ALIF Concept," *Eur Spine J.*, 2000, 9(1): S35-S43.

Mayer and Wiechert, "Microsurgical Anterior Approaches to the Lumbar Spine for Interbody Fusion and Total Disc Replacement," *Neurosurgery*, 2002, 51(2): 159-165.

McAfee et al., "Minimally Invasive Anterior Retroperitoneal Approach to the Lumbar Spine: Emphasis on the Lateral BAK," *Spine*, 1998, 23(13): 1476-1484.

Rao, et al. "Dynamic retraction of the psoas muscle to expose the lumbar spine using the retroperitoneal approach," *J. Neurosurg Spine*, 2006, 5: 468-470.

Wolfla et al., "Retroperitoneal lateral lumbar interbody fusion with titanium threaded fusion cages," *J. Neurosurg (Spine)*, 2002, 96: 50-55.

* cited by examiner

SURGICAL ACCESS SYSTEM AND RELATED METHODS

CROSS-REFERENCES TO RELATED APPLICATIONS

The present application is an non-provisional patent application which claims the benefit of priority from commonly owned and co-pending U.S. Provisional Application Ser. Nos. 60/450,806 (filed Feb. 27, 2003), the entire contents of which is hereby expressly incorporated by reference into this disclosure as if set forth fully herein.

BACKGROUND OF THE INVENTION

I. Field of the Invention

The present invention relates generally to systems and methods for performing surgical procedures and, more particularly, for accessing a surgical target site in order to perform surgical procedures.

II. Discussion of the Prior Art

A noteworthy trend in the medical community is the move away from performing surgery via traditional "open" techniques in favor of minimally invasive or minimal access techniques. Open surgical techniques are generally undesirable in that they typically require large incisions and high amounts of tissue displacement to gain access to the surgical target site, which produces concomitantly high amounts of pain, lengthened hospitalization (increasing health care costs), and high morbidity in the patient population. Less-invasive surgical techniques (including so-called "minimal access" and "minimally invasive" techniques) are gaining favor due to the fact that they involve accessing the surgical target site via incisions of substantially smaller size with greatly reduced tissue displacement requirements. This, in turn, reduces the pain, morbidity and cost associated with such procedures. The access systems developed to date, however, fail in various respects to meet all the needs of the surgeon population.

One drawback associated with prior art surgical access systems relates to the ease with which the operative corridor can be created, as well as maintained over time, depending upon the particular surgical target site. For example, when accessing surgical target sites located beneath or behind musculature or other relatively strong tissue (such as, by way of example only, the psoas muscle adjacent to the spine), it has been found that advancing an operative corridor-establishing instrument directly through such tissues can be challenging and/or lead to unwanted or undesirable effects (such as stressing or tearing the tissues). While certain efforts have been undertaken to reduce the trauma to tissue while creating an operative corridor, such as (by way of example only) the sequential dilation system of U.S. Pat. No. 5,792,044 to Foley et al., these attempts are nonetheless limited in their applicability based on the relatively narrow operative corridor. More specifically, based on the generally cylindrical nature of the so-called "working cannula," the degree to which instruments can be manipulated and/or angled within the cannula can be generally limited or restrictive, particularly if the surgical target site is a relatively deep within the patient.

Efforts have been undertaken to overcome this drawback, such as shown in U.S. Pat. No. 6,524,320 to DiPoto, wherein an expandable portion is provided at the distal end of a cannula for creating a region of increased cross-sectional area adjacent to the surgical target site. While this system may provide for improved instrument manipulation relative to sequential dilation access systems (at least at deep sites within the patient), it is nonetheless flawed in that the deployment of the expandable portion may inadvertently compress or impinge upon sensitive tissues adjacent to the surgical target site. For example, in anatomical regions having neural and/or vasculature structures, such a blind expansion may cause the expandable portion to impinge upon these sensitive tissues and cause neural and/or vasculature compromise, damage and/or pain for the patient.

This highlights yet another drawback with the prior art surgical access systems, namely, the challenges in establishing an operative corridor through or near tissue having major neural structures which, if contacted or impinged, may result in neural impairment for the patient. Due to the threat of contacting such neural structures, efforts thus far have largely restricted to establishing operative corridors through tissue having little or substantially reduced neural structures, which effectively limits the number of ways a given surgical target site can be accessed. This can be seen, by way of example only, in the spinal arts, where the exiting nerve roots and neural plexus structures in the psoas muscle have rendered a lateral or far lateral access path (so-called trans-psoas approach) to the lumbar spine virtually impossible. Instead, spine surgeons are largely restricted to accessing the spine from the posterior (to perform, among other procedures, posterior lumbar interbody fusion (PLIF)) or from the anterior (to perform, among other procedures, anterior lumbar interbody fusion (ALIF)).

Posterior-access procedures involve traversing a shorter distance within the patient to establish the operative corridor, albeit at the price of oftentimes having to reduce or cut away part of the posterior bony structures (i.e. lamina, facets, spinous process) in order to reach the target site (which typically comprises the disc space). Anterior-access procedures are relatively simple for surgeons in that they do not involve reducing or cutting away bony structures to reach the surgical target site. However, they are nonetheless disadvantageous in that they require traversing through a much greater distance within the patient to establish the operative corridor, oftentimes requiring an additional surgeon to assist with moving the various internal organs out of the way to create the operative corridor.

The present invention is directed at eliminating, or at least minimizing the effects of, the above-identified drawbacks in the prior art.

SUMMARY OF THE INVENTION

The present invention accomplishes this goal by providing a novel access system and related methods which involve detecting the existence of (and optionally the distance and/or direction to) neural structures before, during, and after the establishment of an operative corridor through (or near) any of a variety of tissues having such neural structures which, if contacted or impinged, may otherwise result in neural impairment for the patient. It is expressly noted that, although described herein largely in terms of use in spinal surgery, the access system of the present invention is suitable for use in any number of additional surgical procedures wherein tissue having significant neural structures must be passed through (or near) in order to establish an operative corridor.

According to one broad aspect of the present invention, the access system comprises a tissue distraction assembly and a tissue retraction assembly, both of which may be equipped with one or more electrodes for use in detecting the existence of (and optionally the distance and/or direction to) neural structures. The tissue distraction assembly (in conjunction with one or more elements of the tissue retraction assembly) is capable of, as an initial step, distracting a region of tissue between the skin of the patient and the surgical target site. The tissue retraction assembly is capable of, as a secondary step, being introduced into this distracted region to thereby define and establish the operative corridor. Once established, any of a variety of surgical instruments, devices, or implants may be passed through and/or manipulated within the operative corridor depending upon the given surgical procedure. The electrode(s) are capable of, during both tissue distraction and retraction, detecting the existence of (and optionally the distance and/or direction to) neural structures such that the operative corridor may be established through (or near) any of a variety of tissues having such neural structures which, if contacted or impinged, may otherwise result in neural impairment for the patient. In this fashion, the access system of the present invention may be used to traverse tissue that would ordinarily be deemed unsafe or undesirable, thereby broadening the number of manners in which a given surgical target site may be accessed.

The tissue distraction assembly may include any number of components capable of performing the necessary distraction. By way of example only, the tissue distraction assembly may include a K-wire, an initial dilator of split construction, and one or more dilators of traditional (that is, non-split) construction for performing the necessary tissue distraction to receive the remainder of the tissue retractor assembly thereafter. One or more electrodes may be provided on one or more of the K-wire and dilator(s) to detect the presence of (and optionally the distance and/or direction to) neural structures during tissue distraction.

The tissue retraction assembly may include any number of components capable of performing the necessary retraction. By way of example only, the tissue retraction assembly may include one or more retractor blades extending from a handle assembly. The handle assembly may be manipulated to open the retractor assembly; that is, allowing the retractor blades to separate from one another simultaneously to create an operative corridor to the surgical target site. In a preferred embodiment, this is accomplished by maintaining a posterior retractor blade in a fixed position relative to the surgical target site (so as to avoid having it impinge upon any exiting nerve roots near the posterior elements of the spine) while the additional retractor blades (i.e. cephalad-most and caudal-most blades) are moved or otherwise translated away from the posterior retractor blade (and each other) so as to create the operative corridor in a fashion that doesn't infringe upon the region of the exiting nerve roots.

The retractor blades may be optionally dimensioned to receive and direct a rigid shim element to augment the structural stability of the retractor blades and thereby ensure the operative corridor, once established, will not decrease or become more restricted, such as may result if distal ends of the retractor blades were permitted to "slide" or otherwise move in response to the force exerted by the displaced tissue. In a preferred embodiment, only the posterior retractor blade is equipped with such a rigid shim element. In an optional aspect, this shim element may be advanced into the disc space after the posterior retractor blade is positioned, but before the retractor is opened into the fully retracted position. The rigid shim element is preferably oriented within the disc space such that is distracts the adjacent vertebral bodies, which serves to restore disc height. It also preferably advances a sufficient distance within the disc space (preferably past the midline), which serves the dual purpose of preventing post-operative scoliosis and forming a protective barrier (preventing the migration of tissue (such as nerve roots) into the operative field and the inadvertent advancement of instruments outside the operative field).

The retractor blades may optionally be equipped with a mechanism for transporting or emitting light at or near the surgical target site to aid the surgeon's ability to visualize the surgical target site, instruments and/or implants during the given surgical procedure. According to one embodiment, this mechanism may comprise, but need not be limited to, providing one or more strands of fiber optic cable within the walls of the retractor blades such that the terminal (distal) ends are capable of emitting light at or near the surgical target site. According to another embodiment, this mechanism may comprise, but need not be limited to, constructing the retractor blades of suitable material (such as clear polycarbonate) and configuration such that light may be transmitted generally distally through the walls of the retractor blade light to shine light at or near the surgical target site. This may be performed by providing the retractor blades having light-transmission characteristics (such as with clear polycarbonate construction) and transmitting the light almost entirely within the walls of the retractor blade (such as by frosting or otherwise rendering opaque portions of the exterior and/or interior) until it exits a portion along the interior (or medially-facing) surface of the retractor blade to shine at or near the surgical target site. The exit portion may be optimally configured such that the light is directed towards the approximate center of the surgical target site and may be provided along the entire inner periphery of the retractor blade or one or more portions therealong.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DESCRIPTION OF THE PREFERRED EMBODIMENT

Figure 1:
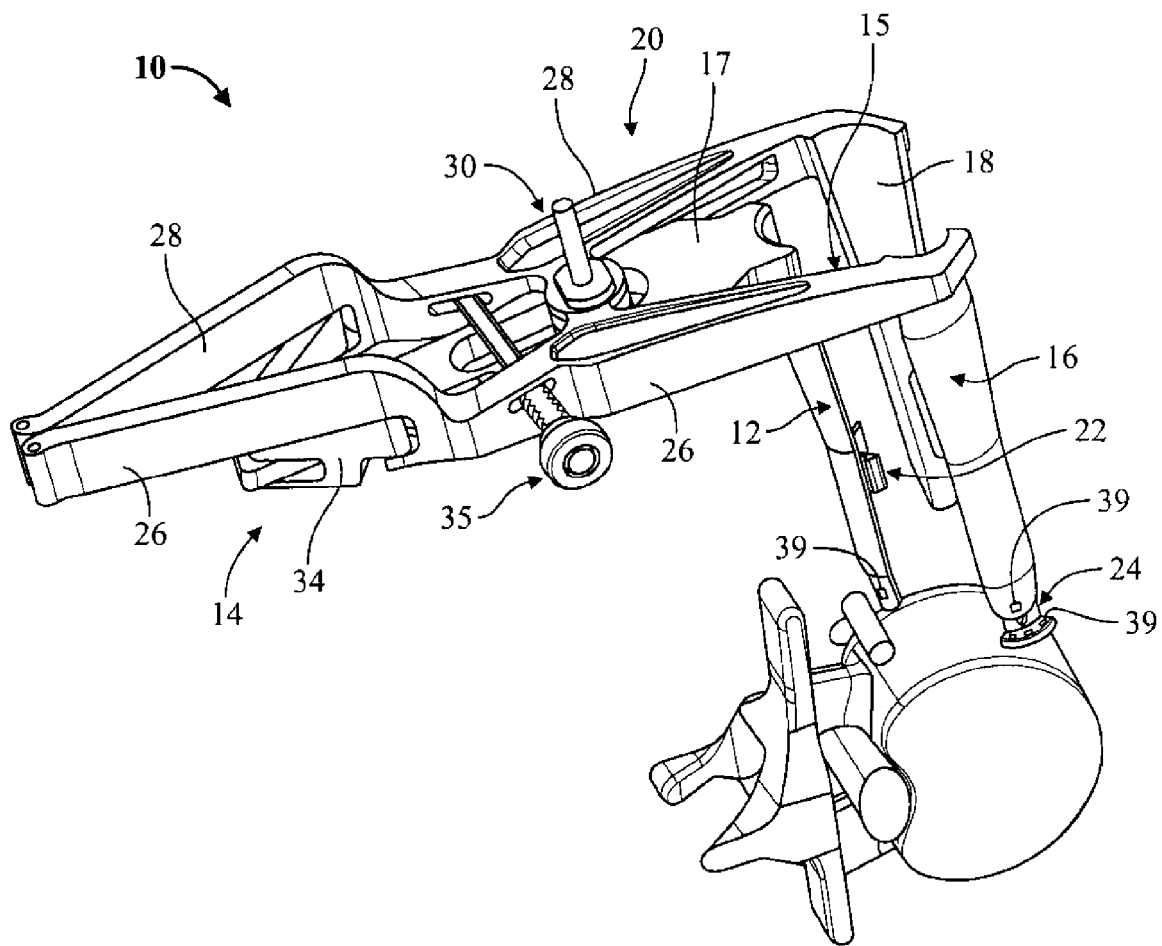
FIG. 1 is a perspective view of a tissue retraction assembly (in use) forming part of a surgical access system according to the present invention.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. It is furthermore to be readily understood that, although discussed below primarily within the context of spinal surgery, the surgical access system of the present invention may be employed in any number of anatomical settings to provide access to any number of different surgical target sites throughout the body. The surgical access system disclosed herein boasts a variety of inventive features and components that warrant patent protection, both individually and in combination.

The present invention involves accessing a surgical target site in a fashion less invasive than traditional "open" surgeries and doing so in a manner that provides access in spite of the neural structures required to be passed through (or near) in order to establish an operative corridor to the surgical target site. Generally speaking, the surgical access system of the present invention accomplishes this by providing a tissue distraction assembly and a tissue retraction assembly, both of which may be equipped with one or more electrodes for use in detecting the existence of (and optionally the distance and/or direction to) neural structures.

These electrodes are preferably provided for use with a nerve surveillance system such as, by way of example, the type shown and described in co-pending and commonly assigned Int'l Patent Application Ser. No. filed Sep. 25, 2002 (claiming priority to U.S. Provisional App. Ser. No. 60/325, 424 filed on Sep. 25, 2001), the entire contents of which are expressly incorporated by reference as if set forth herein in their entirety ("the '424 PCT"). Generally speaking, this nerve surveillance system is capable of detecting the existence of (and optionally the distance and/or direction to) neural structures during the distraction and retraction of tissue by detecting the presence of nerves by applying a stimulation signal to such instruments and monitoring the evoked EMG signals from the myotomes associated with the nerves being passed by the distraction and retraction systems of the present invention. In so doing, the system as a whole (including the surgical access system of the present invention) may be used to form an operative corridor through (or near) any of a variety of tissues having such neural structures, particularly those which, if contacted or impinged, may otherwise result in neural impairment for the patient. In this fashion, the access system of the present invention may be used to traverse tissue that would ordinarily be deemed unsafe or undesirable, thereby broadening the number of manners in which a given surgical target site may be accessed.

The tissue distraction assembly of the present invention (comprising a K-wire, an initial dilator, and a split-dilator disposed within the initial dilator) is employed to distract the tissues extending between the skin of the patient and a given surgical target site (preferably along the posterior region of the target intervertebral disc). A secondary distraction assembly (i.e. a plurality of sequentially dilating cannulae) may optionally be employed after the initial distraction assembly to further distract the tissue. Once distracted, the resulting void or distracted region within the patient is of sufficient size to accommodate a tissue retraction assembly of the present invention. More specifically, the tissue retraction assembly (comprising a plurality of retractor blades extending from a handle assembly) may be advanced relative to the secondary distraction assembly such that the retractor blades, in a first, closed position, are advanced over the exterior of the secondary distraction assembly. At that point, the handle assembly may be operated to move the retractor blades into a second, open or "retracted" position to create an operative corridor to the surgical target site.

According to one aspect of the invention, following (or before) this retraction, a posterior shim element (which is preferably slideably engaged with the posterior retractor blade) may be advanced such that a distal shim extension in positioned within the posterior region of the disc space. If done before retraction, this helps ensure that the posterior retractor blade will not move posteriorly during the retraction process, even though the other retractor blades (i.e. cephalad-most and caudal-most) are able to move and thereby create an operative corridor. Fixing the posterior retractor blade in this fashion serves several important functions. First, the distal end of the shim element serves to distract the adjacent vertebral bodies, thereby restoring disc height. It also rigidly couples the posterior retractor blade in fixed relation relative to the vertebral bodies. The posterior shim element also helps ensure that surgical instruments employed within the operative corridor are incapable of being advanced outside the operative corridor, preventing inadvertent contact with the exiting nerve roots during the surgery. Once in the appropriate retracted state, the cephalad-most and caudal-most retractor blades may be locked in position and, thereafter, retractor extenders advanced therealong to prevent the ingress or egress of instruments or biological structures (i.e. nerves, vasculature, etc. . . . ) into or out of the operative corridor. Once the operative corridor is established, any of a variety of surgical instruments, devices, or implants may be passed through and/or manipulated within the operative corridor depending upon the given surgical procedure.

FIG. 1 illustrates a tissue retraction assembly 10 forming part of a surgical access system according to the present invention. The retraction assembly 10 includes a plurality of retractor blades extending from a handle assembly 20. By way of example only, the handle assembly 20 is provided with a posterior retractor blade 12, a cephalad-most retractor blade 16, and a caudal-most retractor blade 18. Although shown and described below with regard to the three-bladed configuration, it is to be readily appreciated that the number of retractor blades may be increased or decreased without departing from the scope of the present invention. The retractor assembly 10 is shown in a fully retracted or "open" configuration, with the retractor blades 12, 16, 18 positioned a distance from one another so as to form an operative corridor 15 there between and extending to a surgical target site (i.e. an annulus of an intervertebral disc).

The retractor blades 12, 16, 18 may be equipped with various additional features or components. By way of example only, posterior retractor blade 12 may be equipped with a shim element 22 (shown more clearly in FIG. 15). Shim element 22 serves to distract the adjacent vertebral bodies (thereby restoring disc height), helps secure the retractor assembly 10 relative to the surgical target site, and forms a protective barrier to prevent the ingress or egress of instruments or biological structures (i.e. nerves, vasculature, etc. . . . ) into or out of the operative corridor. Each of the remaining retractor blades (cephalad-most blade 16 and caudal-most blade 18) may be equipped with a retractor extender 24 (shown more clearly in FIG. 16). The retractor extenders 24 extend from the cephalad-most and caudal-most retractor blades 16, 18 to form a protective barrier to prevent the ingress or egress of instruments or biological structures (i.e. nerves, vasculature, etc. . . . ) into or out of the operative corridor.

According to the present invention, any or all of the retractor blades 12, 16, 18, the shim element 22 and/or the retractor extender 24 may be provided with one or more electrodes 39 (preferably at their distal regions) equipped for use with a nerve surveillance system, such as, by way of example, the type shown and described in the NeuroVision PCT Applications set forth below.

The handle assembly 20 may be coupled to any number of mechanisms for rigidly registering the handle assembly 20 in fixed relation to the operative site, such as through the use of an articulating arm mounted to the operating table. The handle assembly 20 includes first and second arm members 26, 28 hingedly coupled via coupling mechanism 30 (i.e. bolt/nut combination disposed through receiving apertures formed along arm members 26, 28). The cephalad-most retractor blade 16 is rigidly coupled (generally perpendicularly) to the end of the first arm member 26. The caudal-most retractor blade 18 is rigidly coupled (generally perpendicularly) to the end of the second arm member 28. With combined reference to FIG. 10, the posterior retractor blade 12 is rigidly coupled (generally perpendicularly to) a translating member 17, which is coupled to the handle assembly 20 via a linkage assembly 14. The linkage assembly 14 includes a first link 34 hingedly disposed between the translating member 17 and a point along the first arm member 26 of the handle assembly 20, and a second link 36 hingedly disposed between the translating member 17 and the second arm member 28 of the handle assembly 20. The translating member 17 includes a translation slot 19 through the bolt/nut combination of the coupling mechanism 30 may engage. In use, a user can squeeze the proximal ends of the arms 26, 28 and thereby cause the coupling mechanism 30 to translate distally within the slot 19, which increases the relative distance between the posterior retractor blade 12 and the cephalad-most and caudal-most retractor blades 16, 18. This squeezing motion of the arms 26, 28 simultaneously causes the cephalad-most and caudal-most retractor blades 16, 18 to move away from one another. Taken collectively, the diameter of the operative corridor 15 increases at approximately the same time. An optional locking mechanism 35 (i.e. bolt and nut combination extending between arm members 26, 28) may be provided to selectively lock the arm members 26, 28 relative to one another to thus maintain the retractor assembly 10 in the fully retracted position, once achieved.

Figure 2:
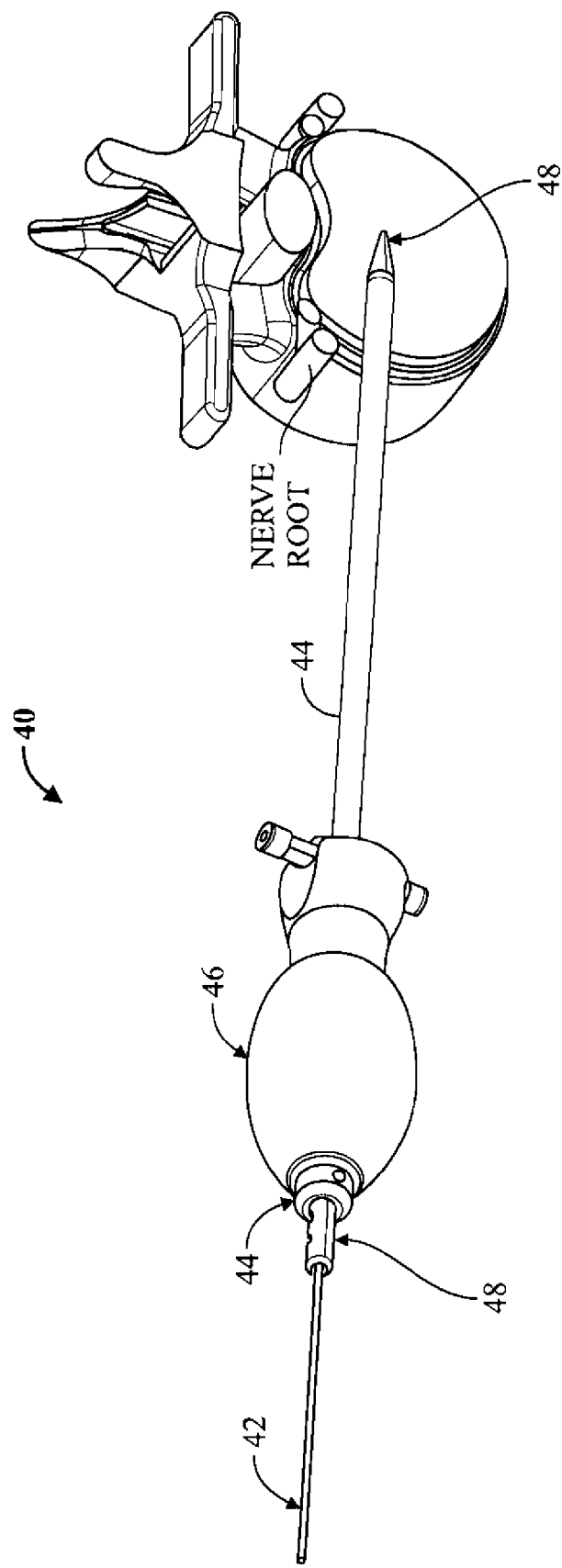
FIG. 2 is a perspective view illustrating the components and use of an initial distraction assembly (i.e. K-wire, an initial dilating cannula with handle, and a split-dilator housed within the initial dilating cannula) forming part of the surgical access system according to the present invention, for use in distracting to a surgical target site (i.e. annulus)
Figure 3:
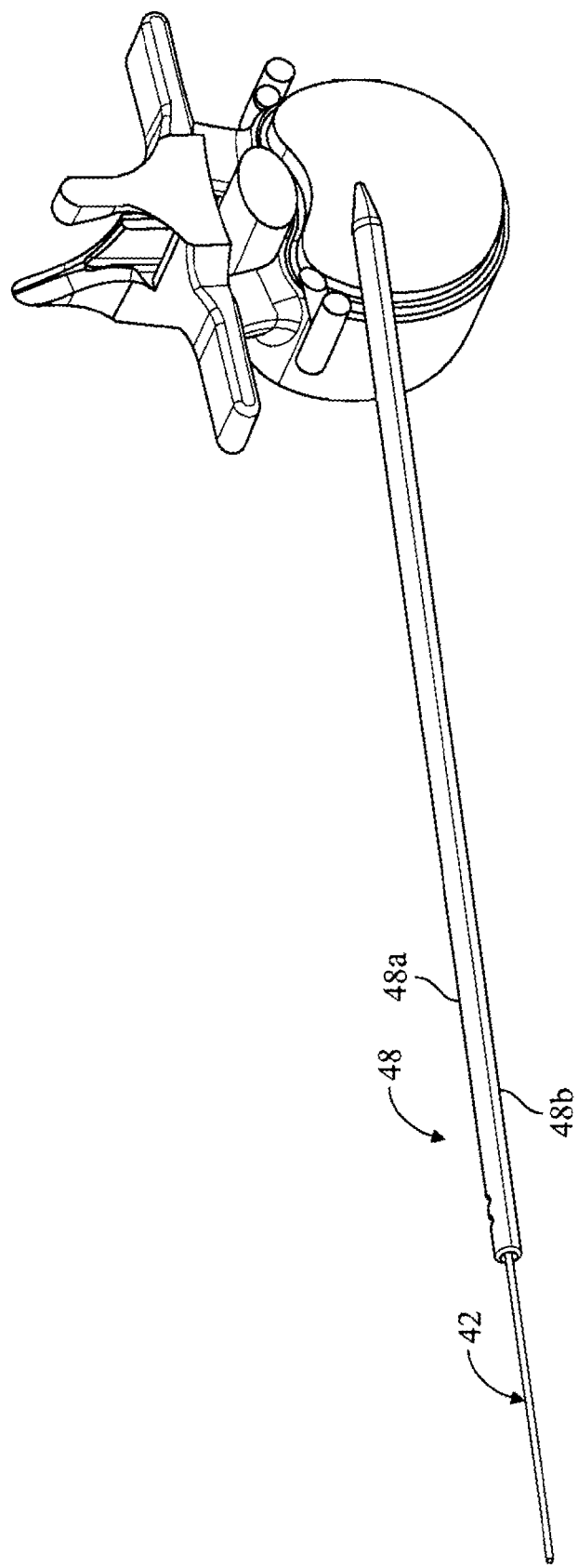
FIG. 3 is a perspective view illustrating the K-wire and split-dilator of the initial distraction assembly with the initial dilating cannula and handle removed.
Figure 4:
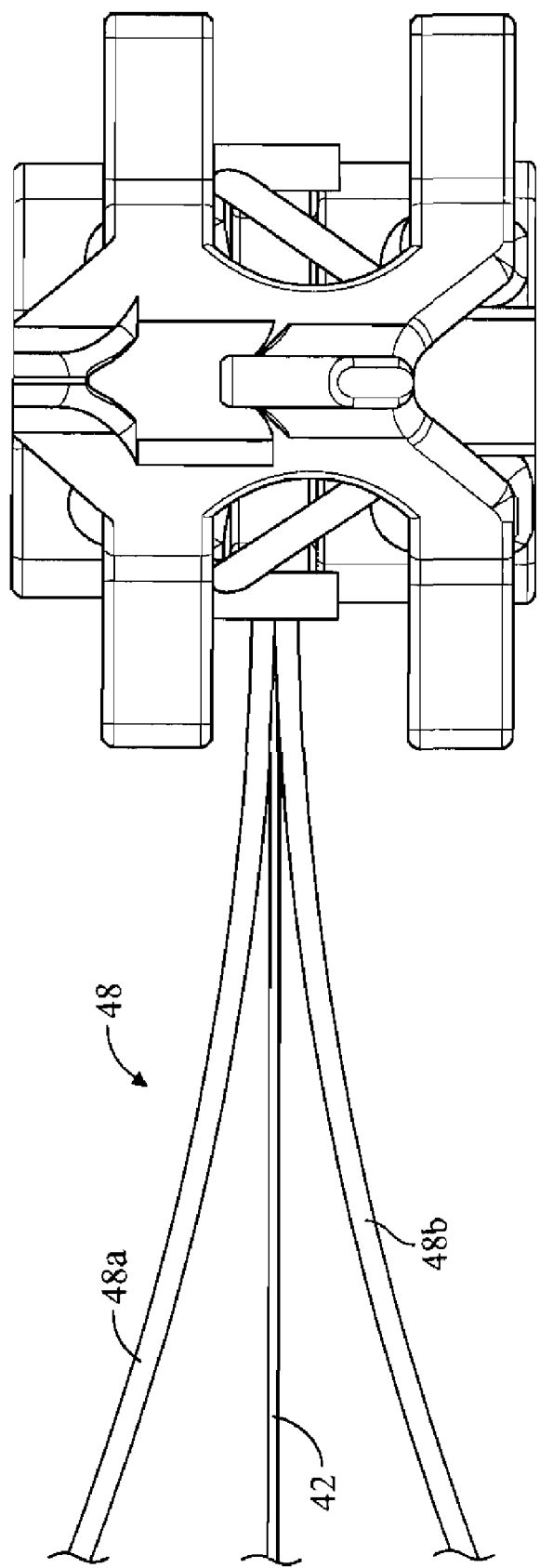
FIG. 4 is a posterior view of the vertebral target site illustrating the split-dilator of the present invention in use distracting in a generally cephalad-caudal fashion according to one aspect of the present invention.

FIG. 2 illustrates an initial distraction assembly 40 forming part of the surgical access system according to the present invention. The initial distraction assembly 40 includes a K-wire 42, an initial dilating cannula 44 with handle 46, and a split-dilator 48 housed within the initial dilating cannula 44. In use, the K-wire 42 and split-dilator 48 are disposed within the initial dilating cannula 44 and the entire assembly 40 advanced through the tissue towards the surgical target site (i.e. annulus). Again, this is preferably accomplished while employing the nerve detection and/or direction features described above. After the initial dilating assembly 40 is advanced such that the distal ends of the split-dilator 48 and initial dilator 44 are positioned within the disc space (FIG. 2), the initial dilator 44 and handle 46 are removed (FIG. 3) to thereby leave the split-dilator 48 and K-wire 42 in place. As shown in FIG. 4, the split-dilator 48 is thereafter split such that the respective halves 48a, 48b are separated from one another to distract tissue in a generally cephalad-caudal fashion relative to the target site. The split dilator 48 may thereafter be relaxed (allowing the dilator halves 48a, 48b to come together) and rotated such that the dilator halves 48a, 48b are disposed in the anterior-posterior plane. Once rotated in this manner, the dilator halves 48a, 48b are again separated to distract tissue in a generally anterior-posterior fashion. Each dilator halve 48a, 48b may be, according to the present invention, provided with one or more electrodes (preferably at their distal regions) equipped for use with a nerve surveillance system, such as, by way of example, the type shown and described in the NeuroVision PCT Applications set forth below.

Figure 5:
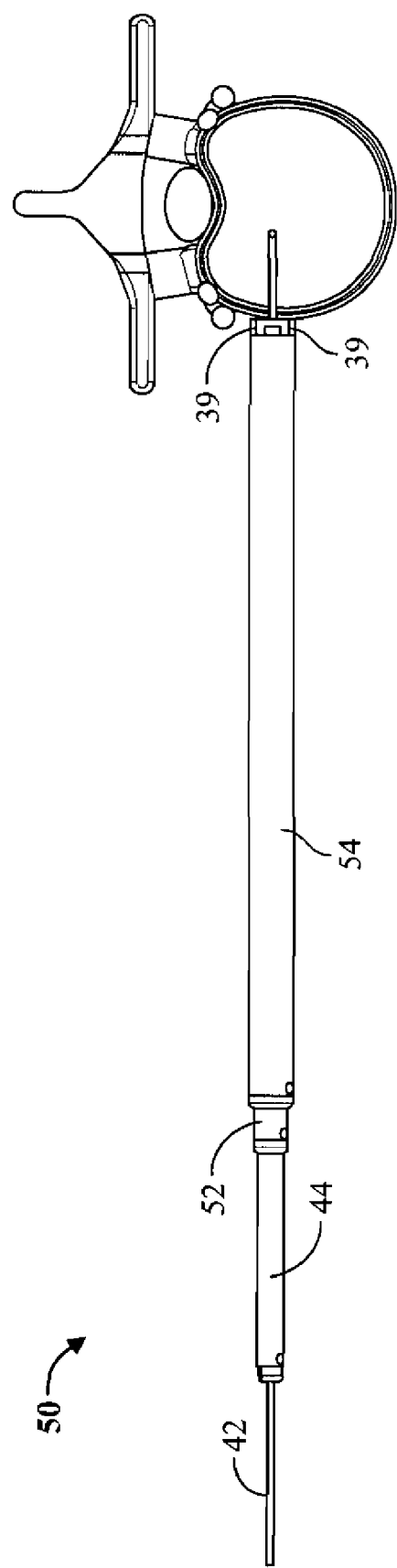
FIG. 5 is a side view illustrating the use of a secondary distraction assembly (comprising a plurality of dilating cannulae over the K-wire) to further distract tissue between the skin of the patient and the surgical target site according to the present invention.

Following this initial distraction, a secondary distraction may be optionally undertaken, such as via a sequential dilation system 50 as shown in FIG. 5. According to the present invention, the sequential dilation system 50 may include the K-wire 42, the initial dilator 44, and one or more supplemental dilators 52, 54 for the purpose of further dilating the tissue down to the surgical target site. Once again, each component of the secondary distraction assembly 50 (namely, the K-wire 42, the initial dilator 44, and the supplemental dilators 52, 54 may be, according to the present invention, provided with one or more electrodes (preferably at their distal regions)

equipped for use with a nerve surveillance system, such as, by way of example, the type shown and described in the NeuroVision PCT Applications set forth below.

Figure 6:
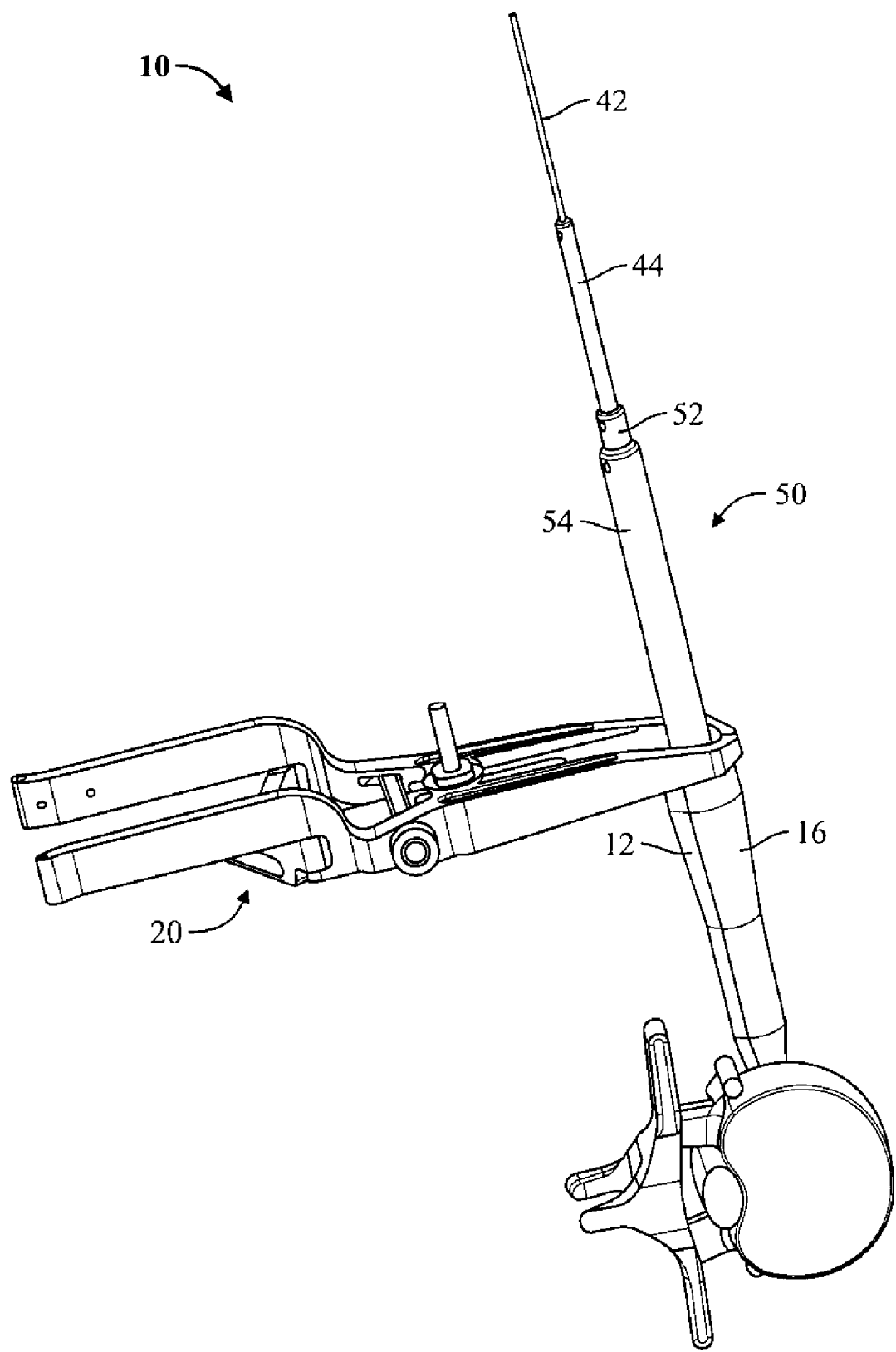
FIGS. 6-7 are perspective and side views, respectively, of a retractor assembly according to the present invention, comprising a handle assembly having three (3) retractor blades extending there from (posterior, cephalad-most, and caudal-most) disposed over the secondary distraction assembly of FIG. 5 (shown in a first, closed position)
Figure 7:
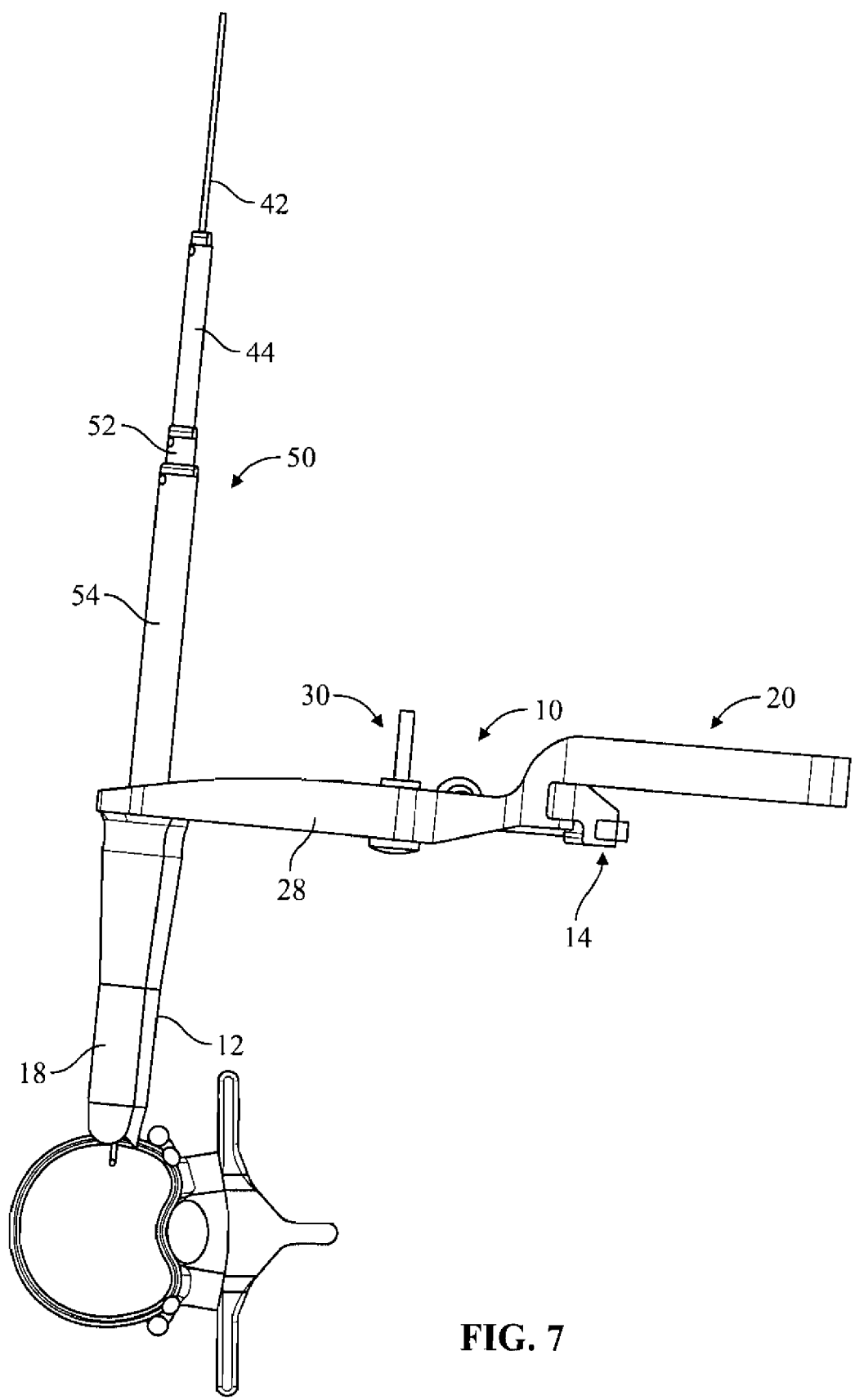
Figure 8:
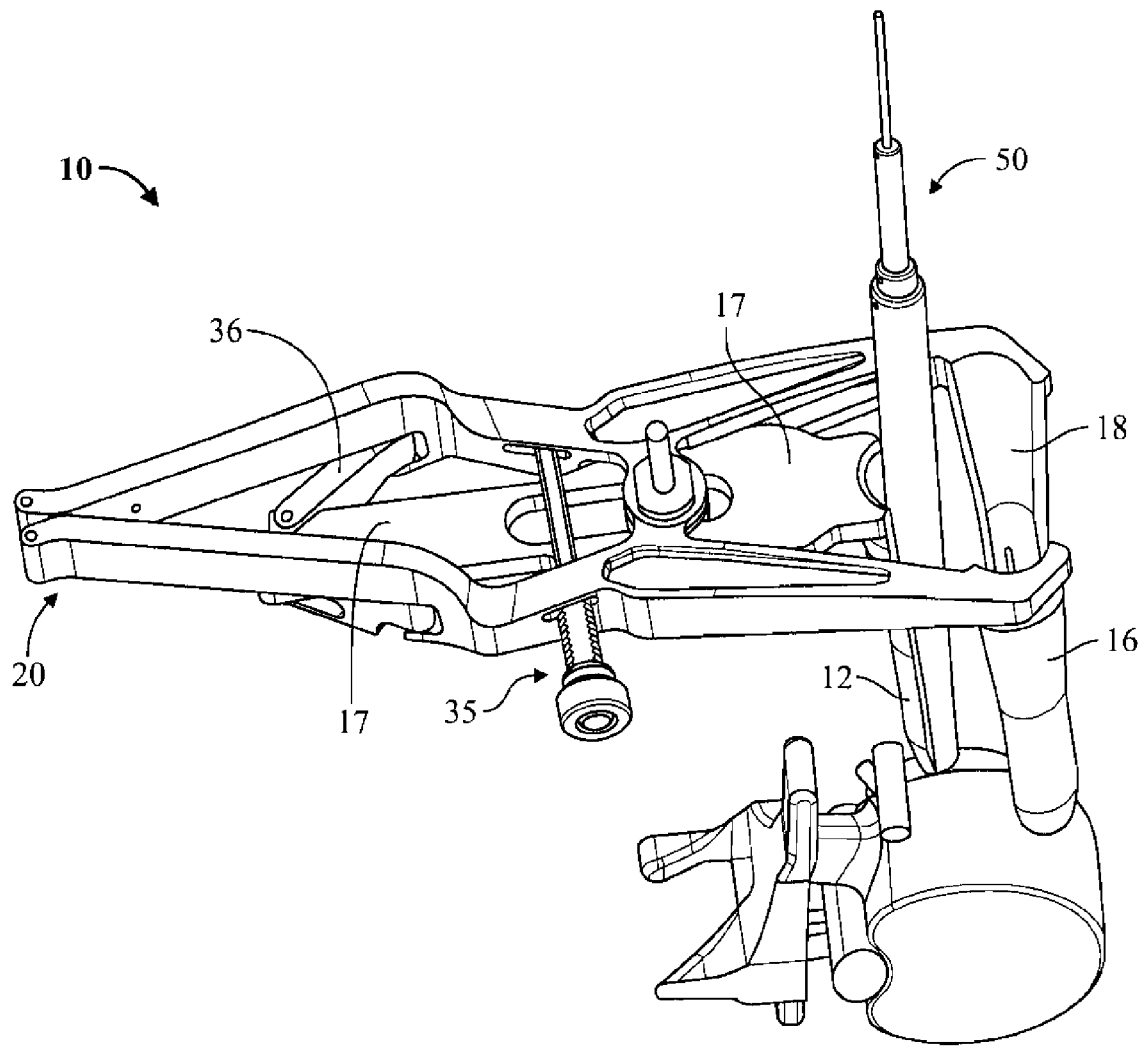
FIGS. 8-10 are perspective, side and top views, respectively, of the retractor assembly of FIGS. 6-7 in a second, opened (i.e. retracted) position (over the secondary distraction assembly) to thereby create an operative corridor to a surgical target site according to the present invention.
Figure 9:
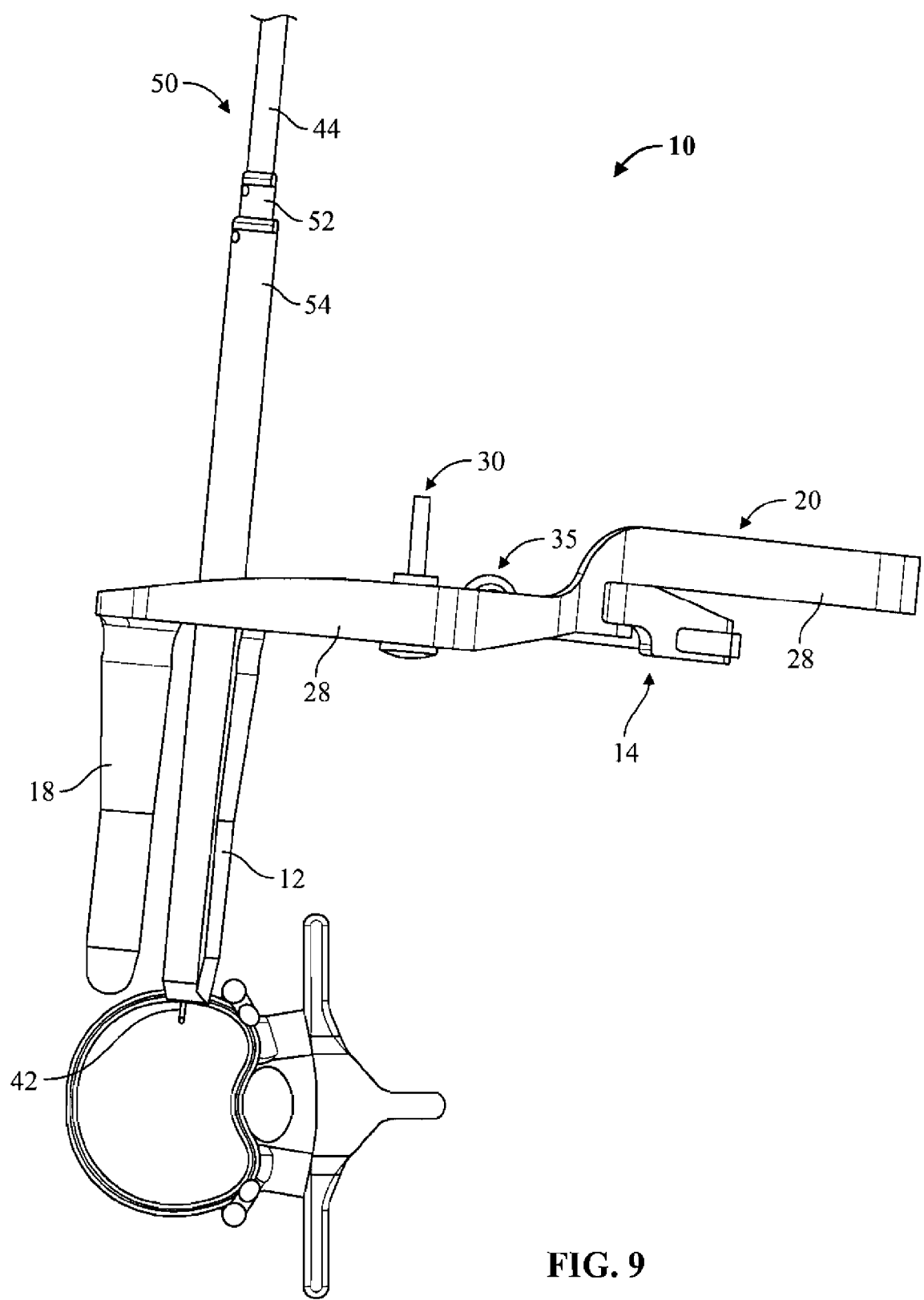
Figure 10:
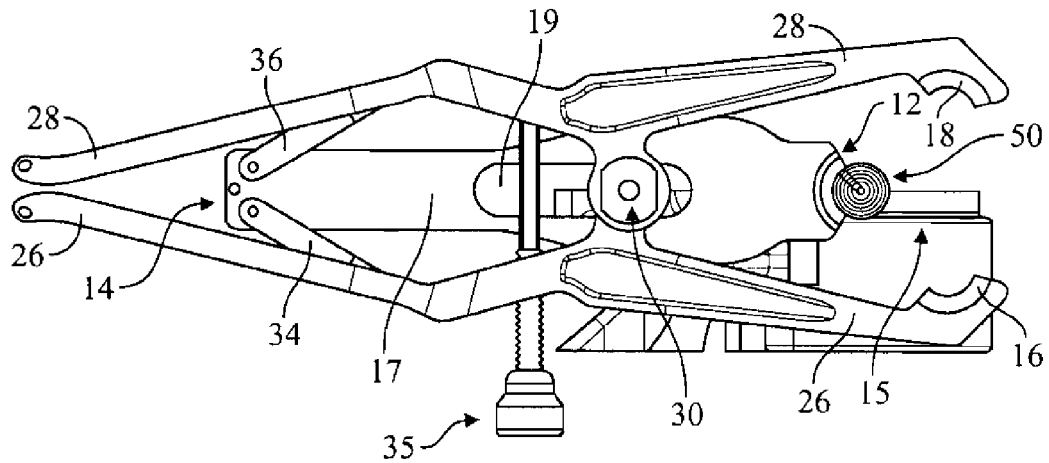
Figure 11:
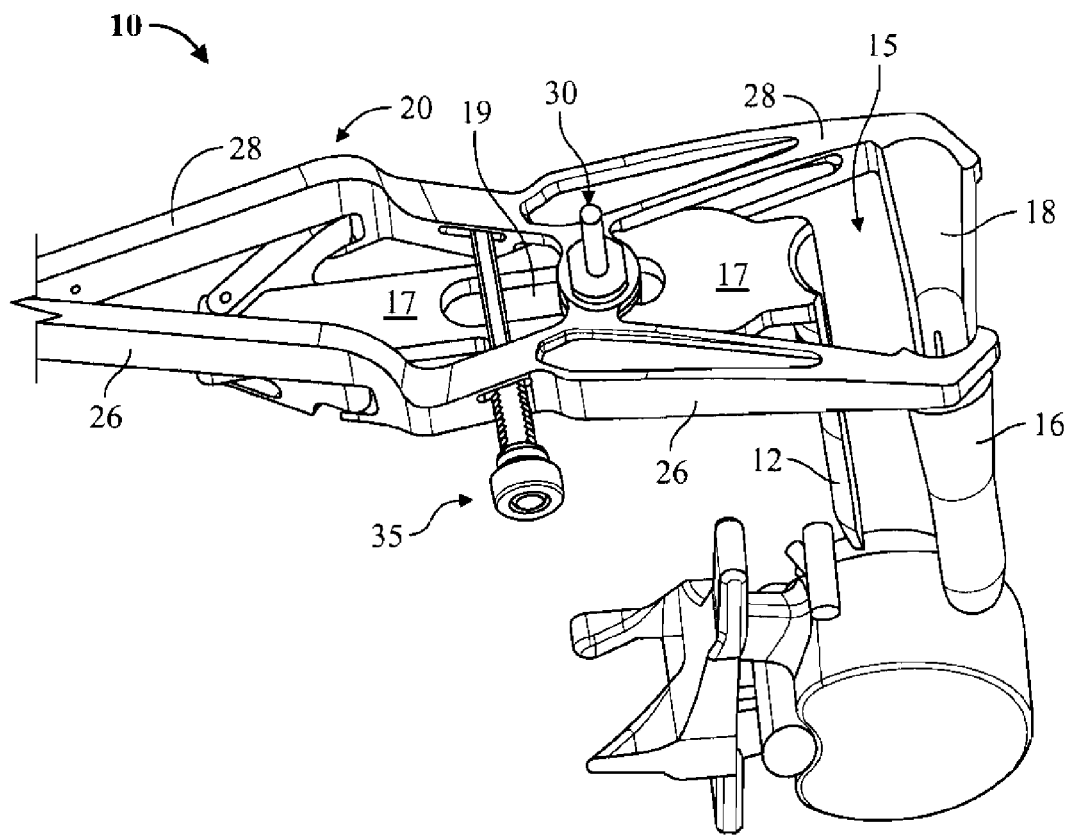
FIGS. 11-13 are perspective, side and top views, respectively, of the retractor assembly of FIGS. 6-7 in the second, opened (i.e. retracted) position (with the secondary distraction assembly removed) illustrating the operative corridor to the surgical target site according to the present invention.
Figure 12:
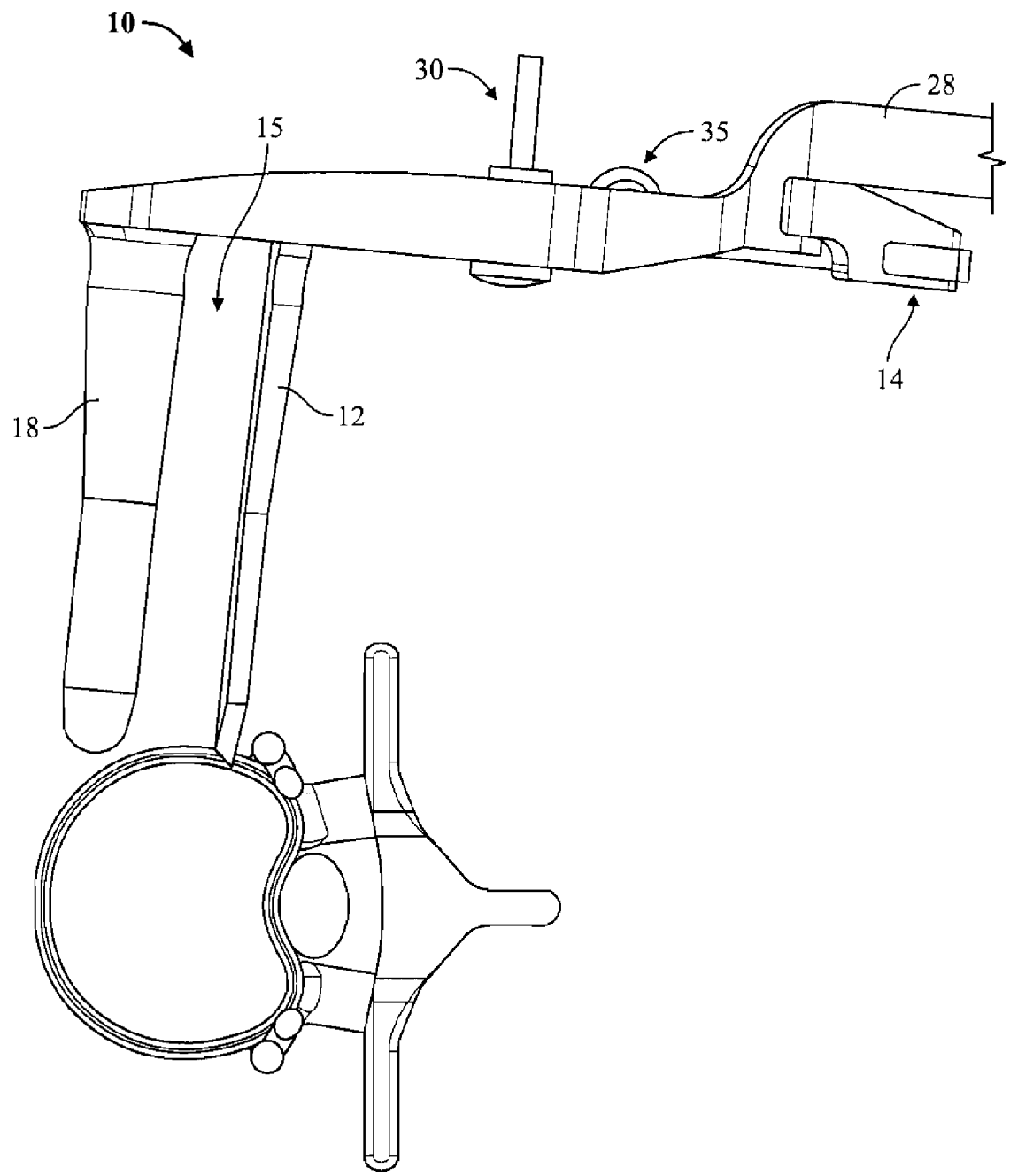
Figure 13:
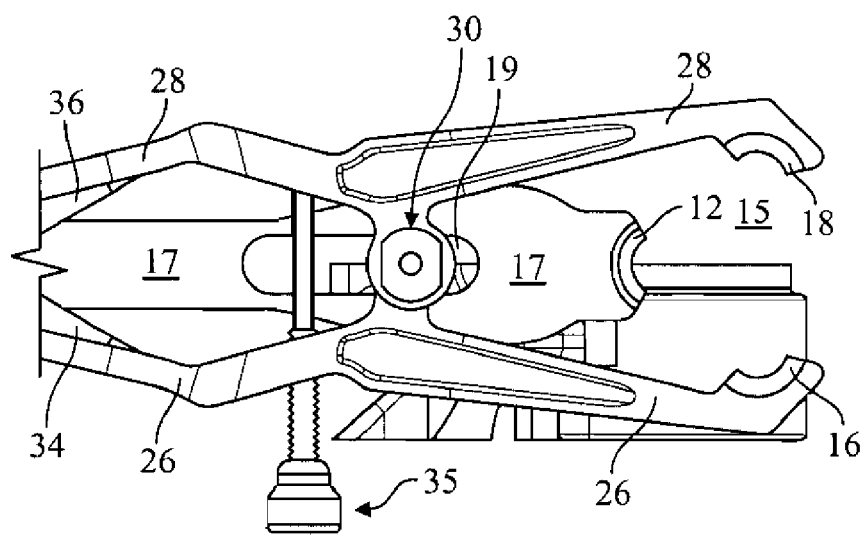

As shown in FIGS. 6-7, the retraction assembly 10 of the present invention is thereafter advanced along the exterior of the sequential dilation system 50. This is accomplished by maintaining the retractor blades 12, 16, 18 in a first, closed position (with the retractor blades 12-16 in generally abutting relation to one another). Once advanced to the surgical target site, the handle assembly 20 may be operated as shown in FIGS. 8-10 to move the retractor blades 12, 16, 18 into a second, open or "retracted" position. As one can see, the posterior retractor blade 12 is allowed to stay in the same general position during this process, such that the cephaladmost and caudal-most retractor blades 14, 16 move away from the posterior retractor blade 12. Again, this is accomplished through the cooperation between the translation member 17 (attached to the posterior retractor blade 12) and the arms 26, 28 of the handle assembly 20 via the linkage assembly 14 and slot 19 in conjunction with the coupling mechanism 30. FIGS. 11-13 illustrate the retractor assembly 10 in the second, opened (i.e. retracted) position (with the secondary distraction assembly 50 removed for clarity) illustrating the operative corridor 15 to the surgical target site according to the present invention.

Figure 14:
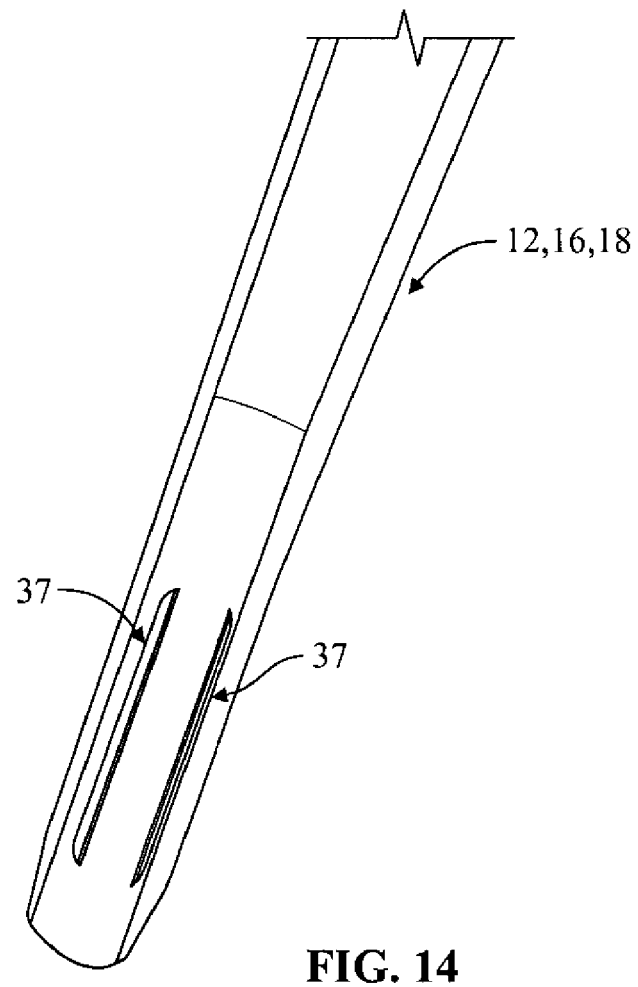
FIG. 14 is an enlarged perspective view of the interior surface of a retractor blade, illustrating a pair of dove-tail grooves dimensioned to engage a shim element (as shown in FIG. 15) and/or a retractor extender (as shown in FIG. 16) according to the present invention.
Figure 16:
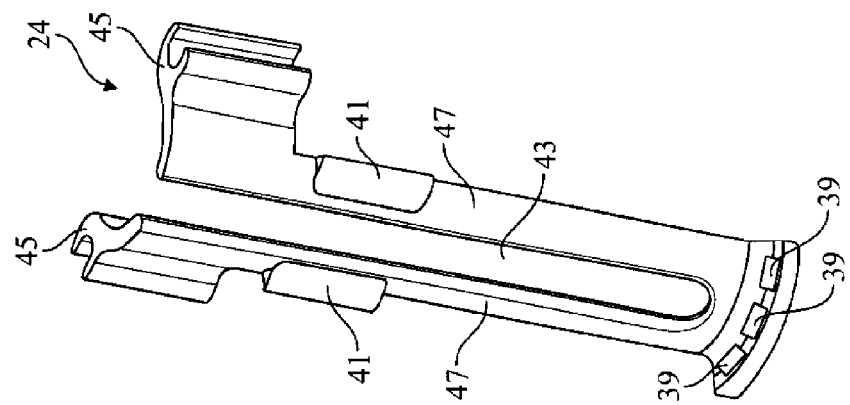
FIG. 16 is a perspective view of a retractor extender dimensioned to be adjustably and removably coupled to a retractor blade (as shown in FIG. 14) according to the present invention.
Figure 15:
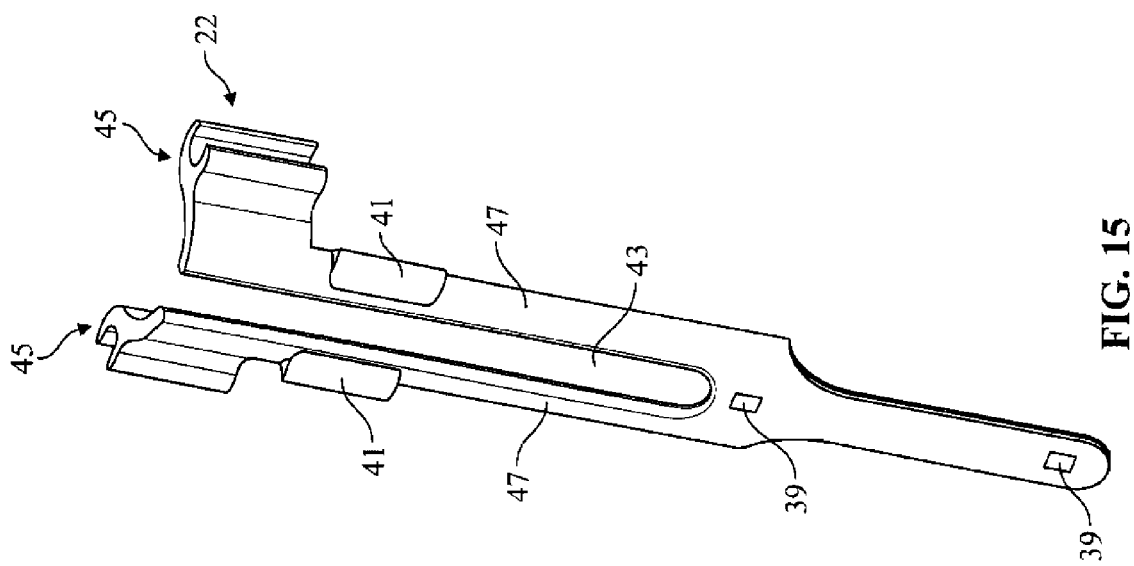
FIG. 15 is a perspective view of a shim element dimensioned to be adjustably and removably coupled to a retractor blade (as shown in FIG. 14) according to the present invention.
Figure 17:
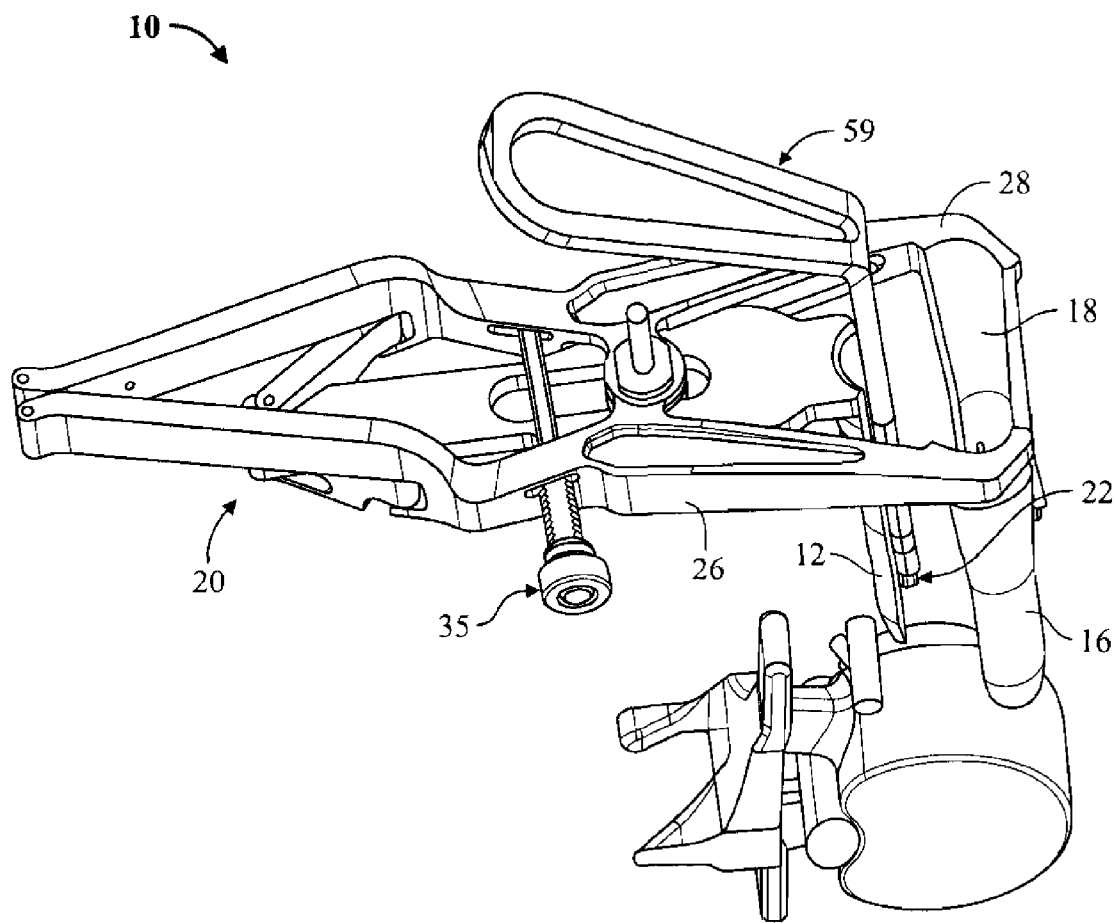
FIGS. 17-18 are perspective and side views, respectively, of the retractor assembly illustrating the use of an introducer device for coupling the shim element of FIG. 15 to the posterior retractor blade and introducing the distal end of the shim (shim extension) into the intradiscal space according to the present invention.
Figure 18:
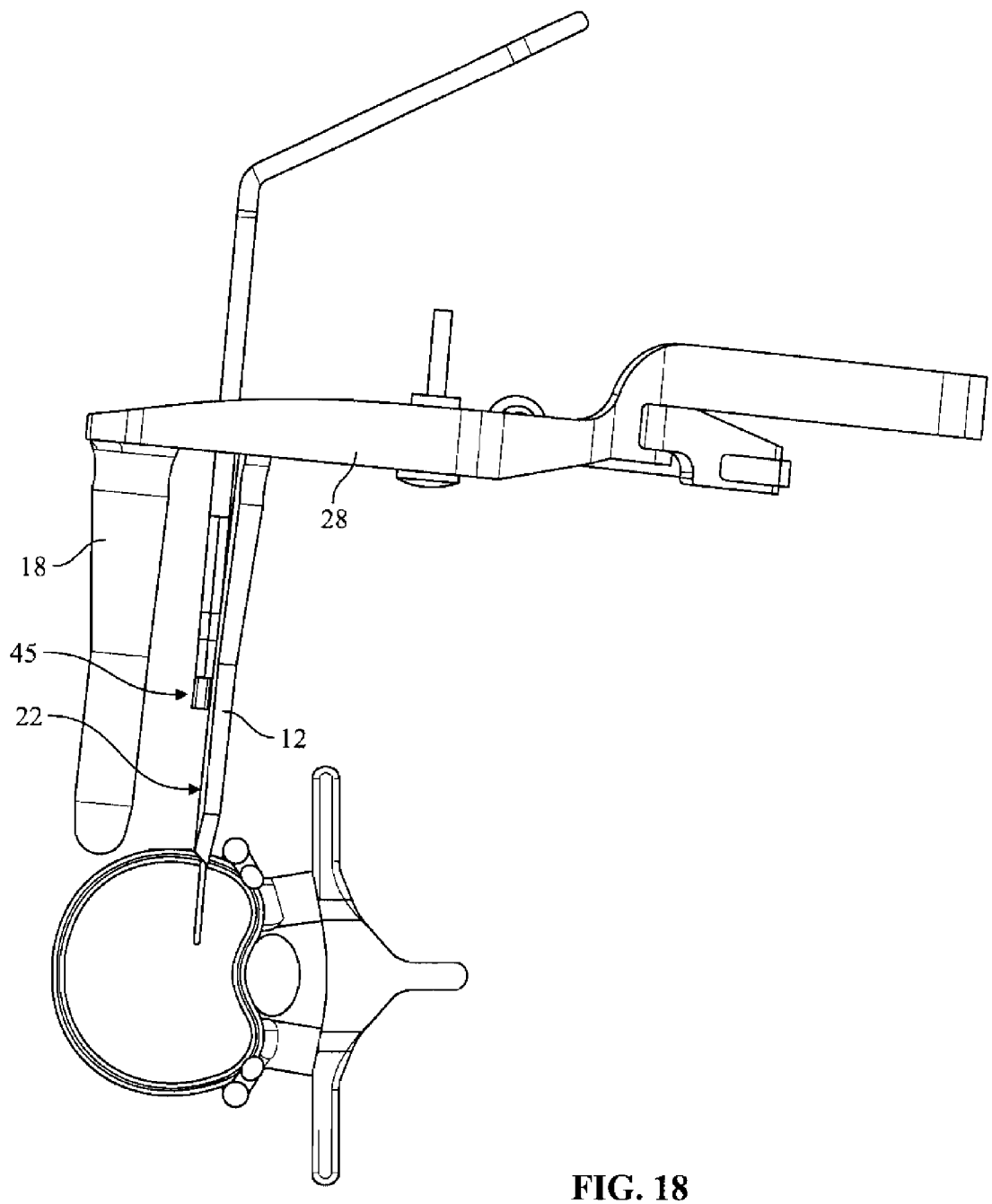
Figure 19:
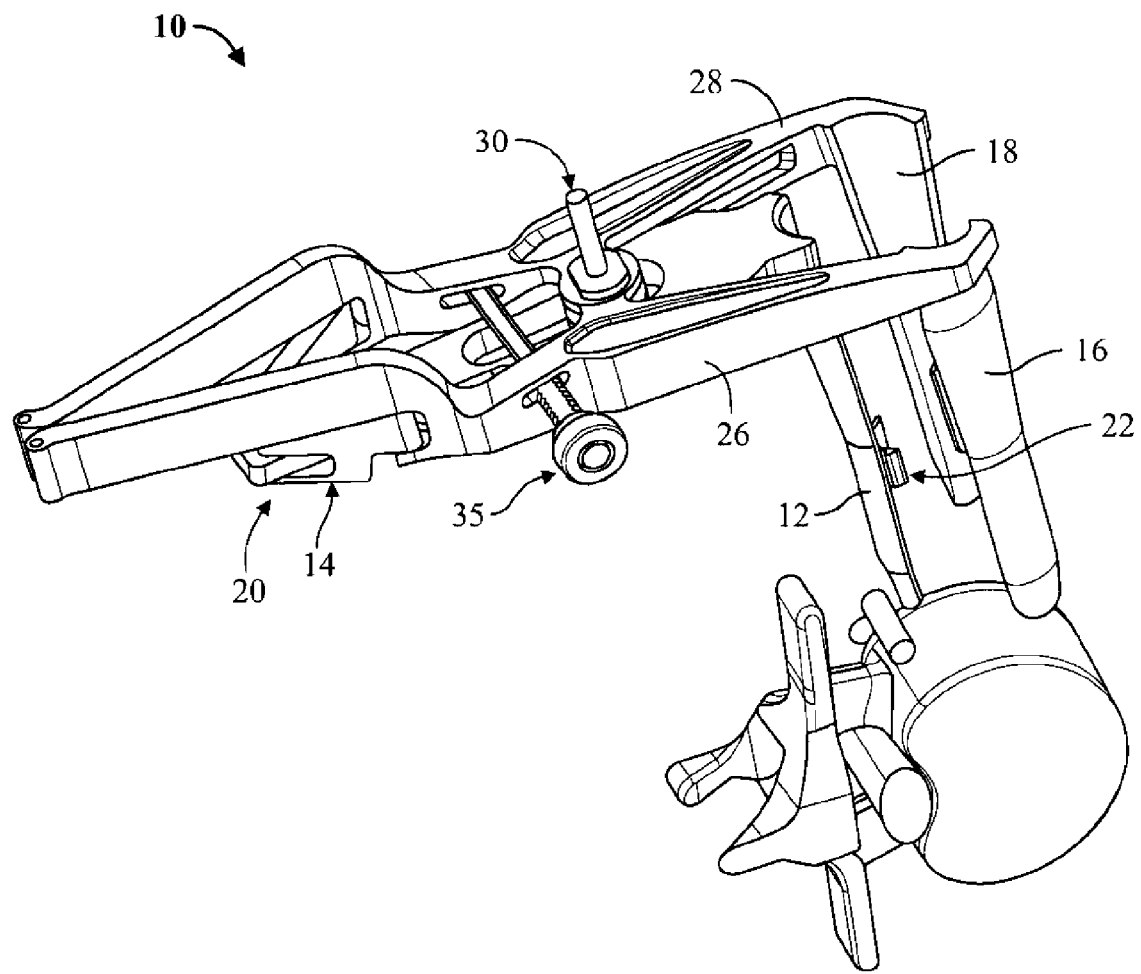
FIGS. 19-21 are perspective, side and top views, respectively, of the retractor assembly illustrating the shim element after introduction according to the present invention.
Figure 20:
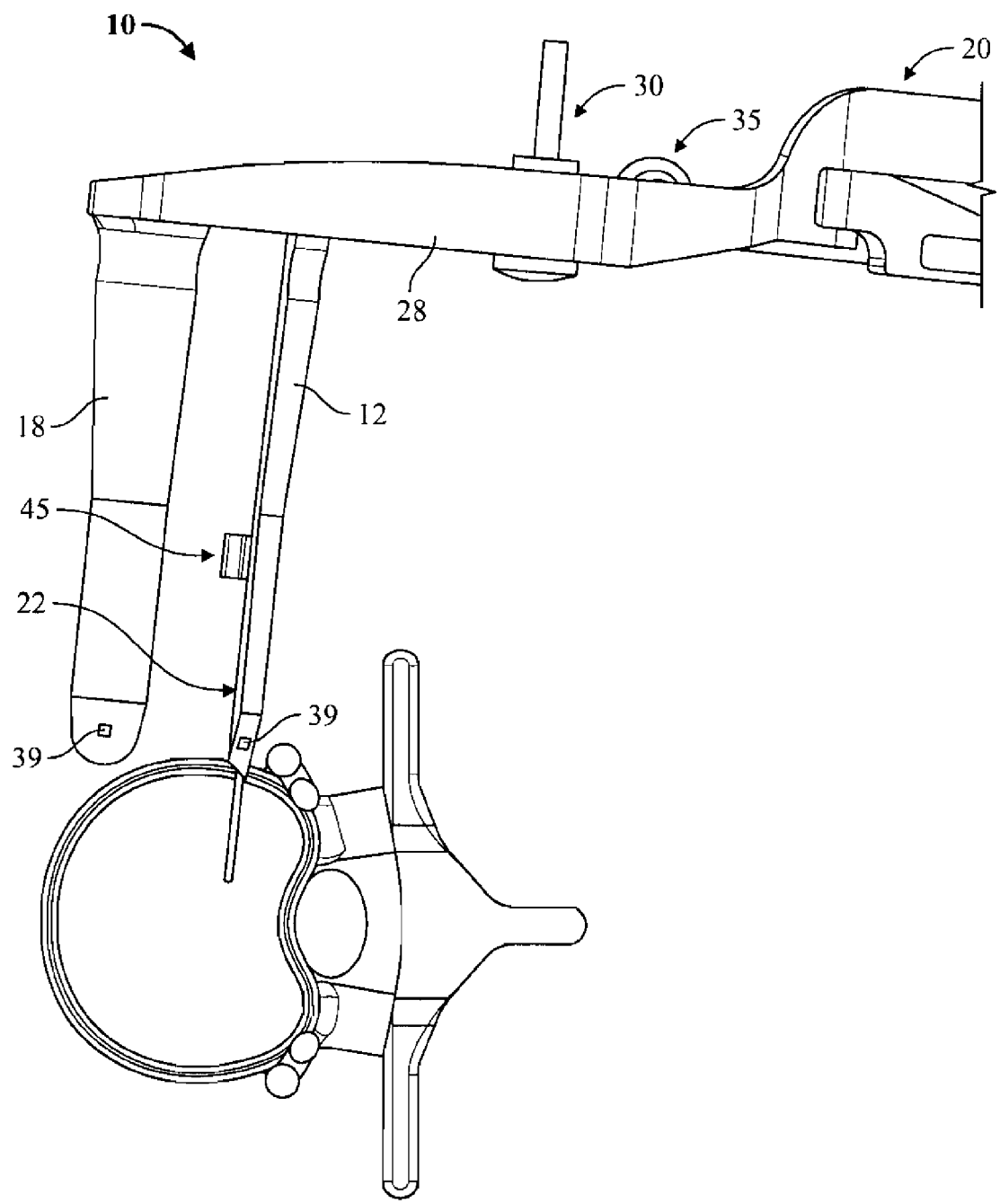
Figure 21:
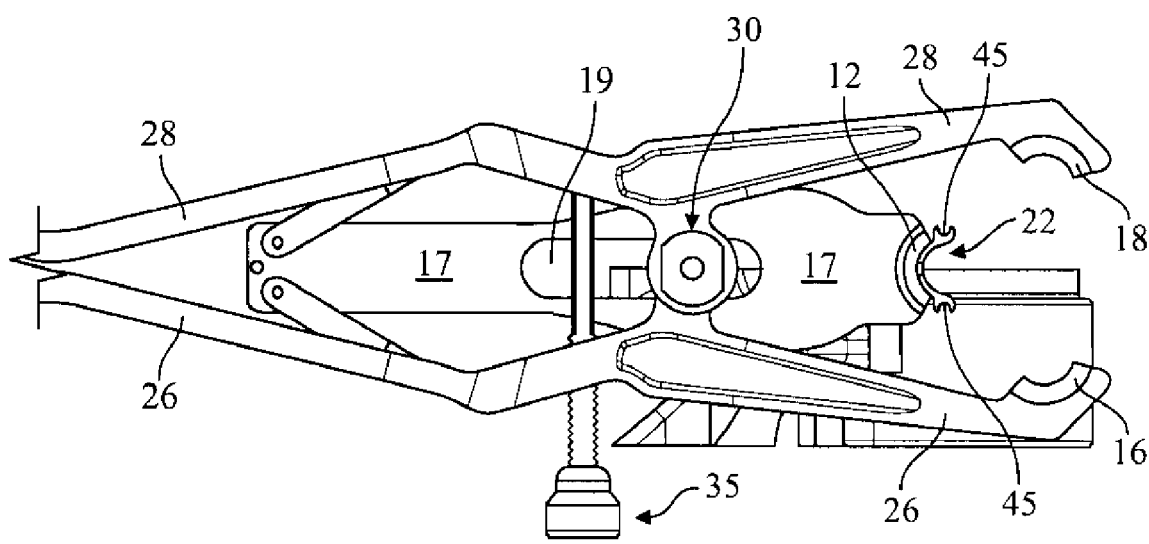
Figure 22:
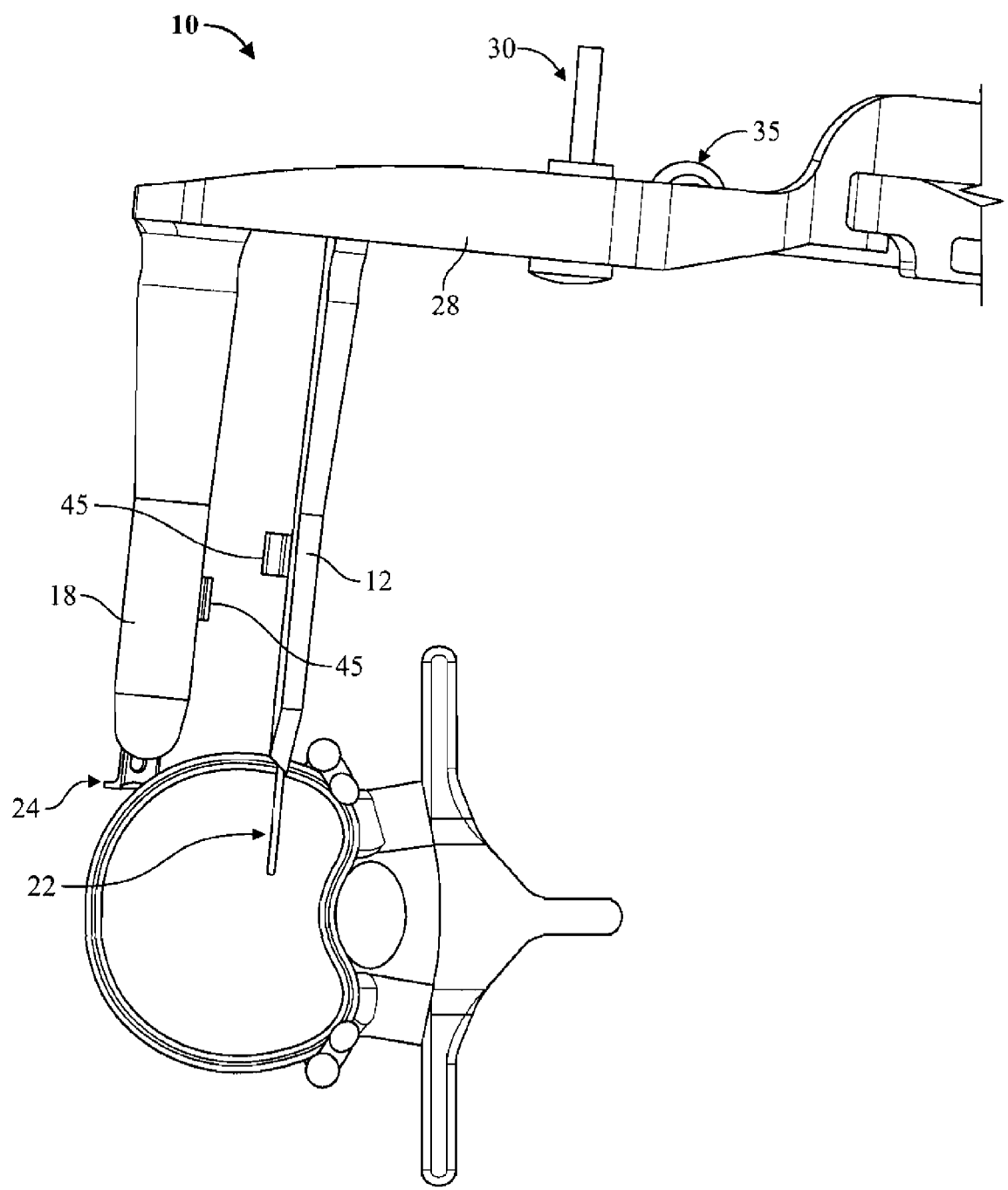
FIG. 22 is a side view of the retractor assembly illustrating the shim element and one of two retractor extenders after introduction according to the present invention.

FIGS. 14-16 illustrate an important aspect of the present invention, wherein (FIG. 15) each retractor blade 12, 16, 18 is provided with a pair of engagement grooves 37 having, by way of example only, a generally dove-tailed cross-sectional shape. The engagement grooves 37 are dimensioned to engage with dove-tail elements 41 provided on the shim element 22 (FIG. 15) and each retractor extender 24 (FIG. 16). In a preferred embodiment, the shim element 22 and retractor extender 24 are each provided with an elongate slot 43 and tool-engaging elements 45. A tool may be used to bias the arms 47 of each device inwardly towards one another (decreasing the width of part or most of the slot 43), which forces the dove-tail elements 41 towards one another. This is shown, by way of example only, in FIGS. 17-18, wherein a tool 59 is used to introduce the shim element 22 into engaged relation with the posterior retractor blade 12. When the shim element 22 has been introduced to a desired position (such as having the distal end extend into the intradiscal space as best shown in FIGS. 18 and 20), the tool 59 may then be disengaged or released from the tool-engaging elements 45 such that the dove-tail elements 41 return to their normal position (being biased outwardly by the resiliency of the arms 47) to thereby secure the shim element 22 relative to the posterior retractor blade 12. FIGS. 19-21 illustrate the shim element 22 after introduction according to the present invention. The same process can be used with the retractor extender 24 shown in FIG. 16 with respect to the cephalad-most and caudal-most retractor blades 16, 18. The end result is shown in FIG. 22 with the retraction assembly 10 of the present invention disposed in position over a surgical target site.

Nerve Surveillance

According to yet another aspect of the present invention, any number of distraction components and/or retraction components (including but not limited to those described herein) may be equipped to detect the presence of (and optionally the distance and/or direction to) neural structures during the steps tissue distraction and/or retraction. This is accomplished by employing the following steps: (1) one or more stimulation electrodes are provided on the various distraction and/or retraction components; (2) a stimulation source (e.g. voltage or current) is coupled to the stimulation electrodes; (3) a stimulation signal is emitted from the stimulation electrodes as the various components are advanced towards or maintained at or near the surgical target site; and (4) the patient is monitored to determine if the stimulation signal causes muscles associated with nerves or neural structures within the tissue to innervate. If the nerves innervate, this may indicate that neural structures may be in close proximity to the distraction and/or retraction components.

Neural monitoring may be accomplished via any number of suitable fashions, including but not limited to observing visual twitches in muscle groups associated with the neural structures likely to found in the tissue, as well as any number of monitoring systems, including but not limited to any commercially available "traditional" electromyography (EMG) system (that is, typically operated by a neurophysiologist. Such monitoring may also be carried out via the surgeon-driven EMG monitoring system shown and described in the following commonly owned and co-pending PCT Applications (collectively "NeuroVision PCT Applications"): PCT App. Ser. No. PCT/US02/22247, entitled "System and Methods for Determining Nerve Proximity, Direction, and Pathology During Surgery," filed on Jul. 11, 2002; PCT App. Ser. No. PCT/US02/30617, entitled "System and Methods for Performing Surgical Procedures and Assessments," filed on Sep. 25, 2002; PCT App. Ser. No. PCT/US02/35047, entitled "System and Methods for Performing Percutaneous Pedicle Integrity Assessments," filed on Oct. 30, 2002; and PCT App. Ser. No. PCT/US03/02056, entitled "System and Methods for Determining Nerve Direction to a Surgical Instrument," filed Jan. 15, 2003. The entire contents of each of the above-enumerated NeuroVision PCT Applications is hereby expressly incorporated by reference into this disclosure as if set forth fully herein.

In any case (visual monitoring, traditional EMG and/or surgeon-driven EMG monitoring), the access system of the present invention may advantageously be used to traverse tissue that would ordinarily be deemed unsafe or undesirable, thereby broadening the number of manners in which a given surgical target site may be accessed.

Figure 23:
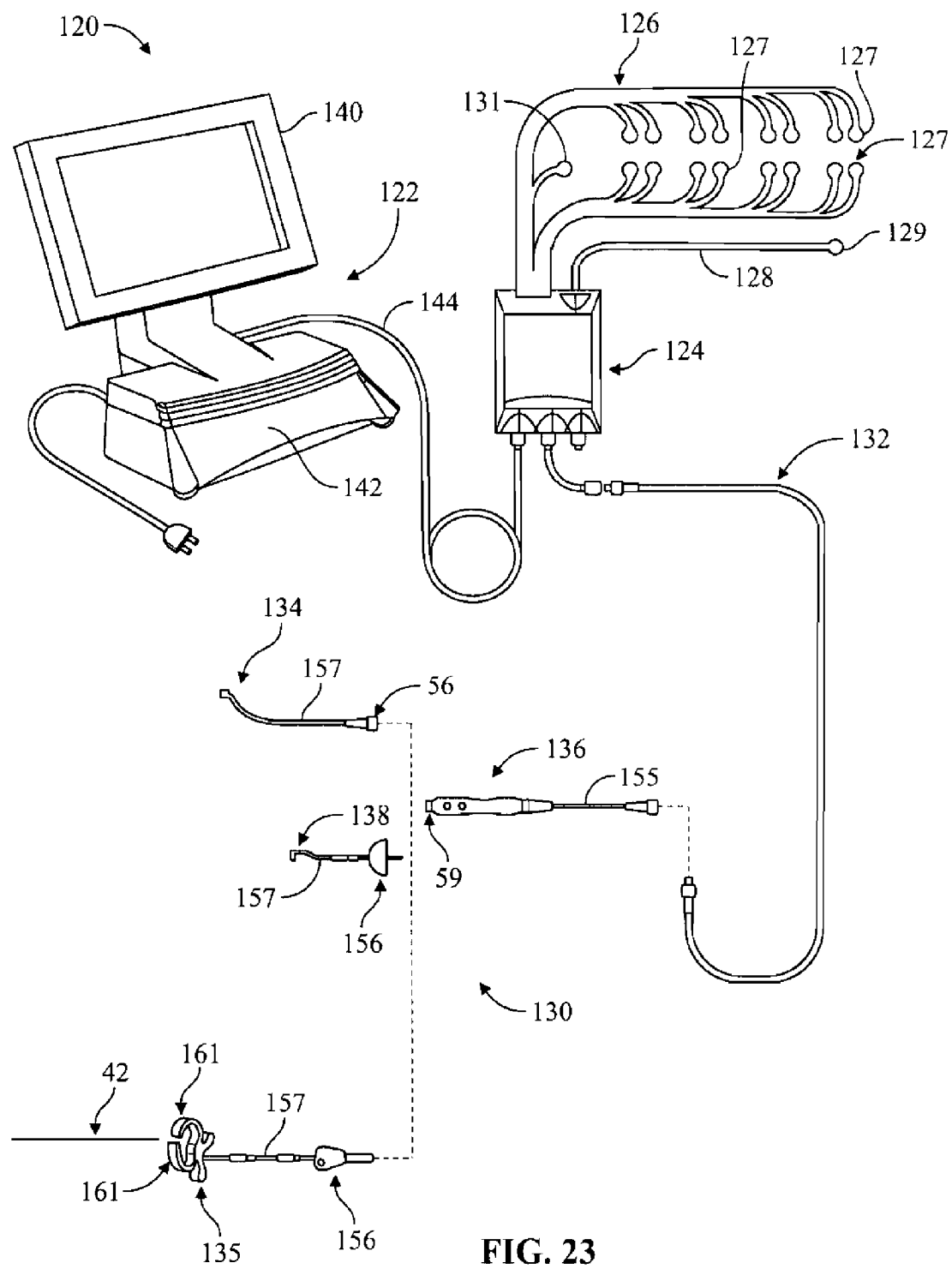
FIG. 23 is a perspective view of an exemplary nerve monitoring system capable of performing nerve monitoring before, during and after the creating of an operative corridor to a surgical target site using the surgical access system in accordance with the present invention.
Figure 24:
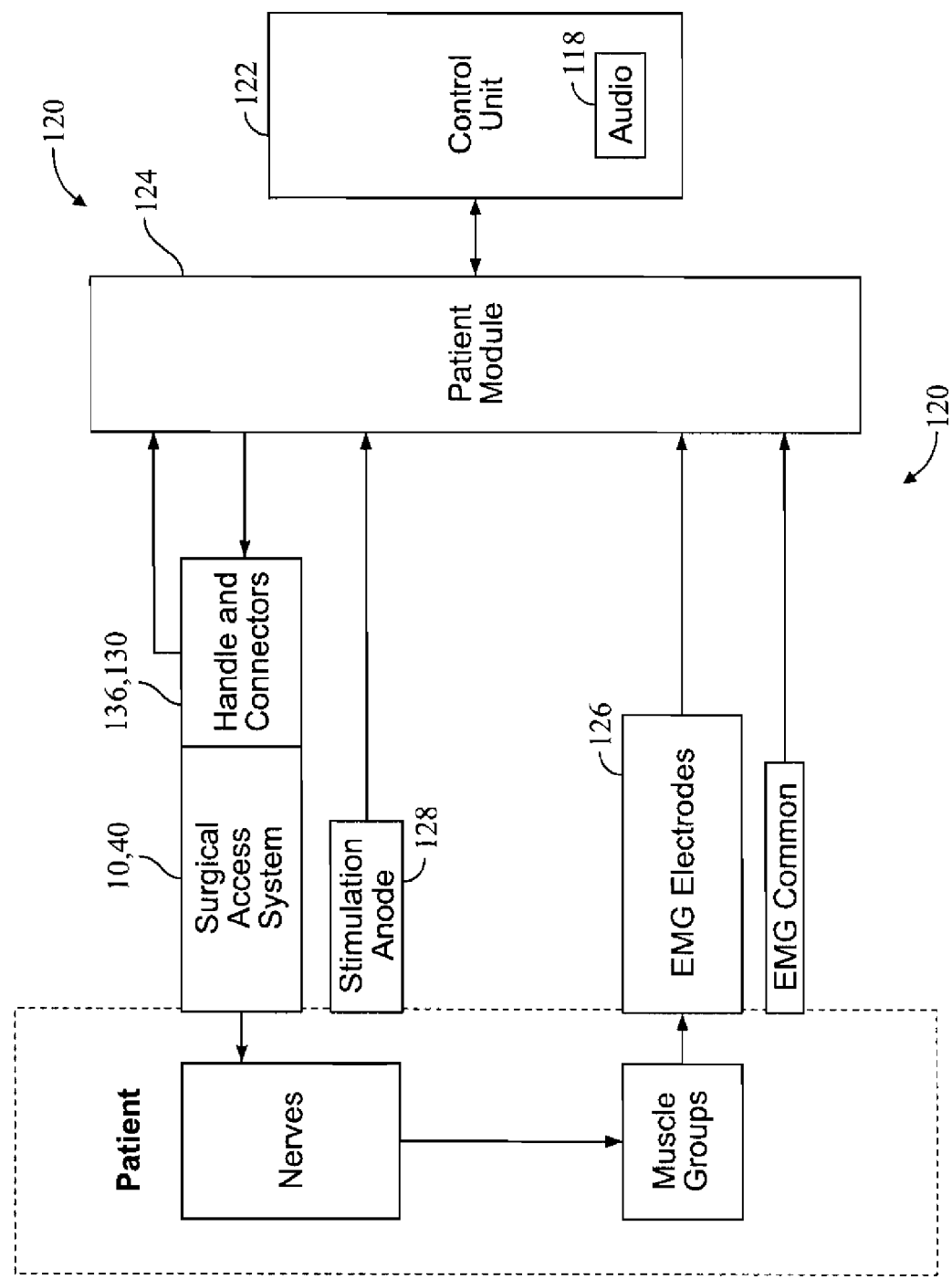
FIG. 24 is a block diagram of the nerve monitoring system shown in FIG. 23.

FIGS. 23-24 illustrate, by way of example only, a monitoring system 120 of the type disclosed in the NeuroVision PCT Applications suitable for use with the surgical access system 10 of the present invention. The monitoring system 120 includes a control unit 122, a patient module 124, and an EMG harness 126 and return electrode 128 coupled to the patient module 124, and a cable 132 for establishing electrical communication between the patient module 124 and the surgical access system 10 (FIG. 1). More specifically, this electrical communication can be achieved by providing, by way of example only, a hand-held stimulation controller 152 capable of selectively providing a stimulation signal (due to the operation of manually operated buttons on the hand-held stimulation controller 152) to one or more connectors 156a, 156b, 156c. The connectors 156a, 156b, 156c are suitable to establish electrical communication between the hand-held stimulation controller 152 and (by way of example only) the stimulation electrodes on the K-wire 42, the dilators 44, 52, 54, the retractor blades 12, 16, 18 and/or the shim elements 22, 24 (collectively "surgical access instruments").

In order to use the monitoring system 120, then, these surgical access instruments must be connected to the connectors 156a, 156b and/or 156c, at which point the user may selectively initiate a stimulation signal (preferably, a current signal) from the control unit 122 to a particular surgical access instruments. Stimulating the electrode(s) on these surgical access instruments before, during and/or after establishing operative corridor will cause nerves that come into close or relative proximity to the surgical access instruments to depolarize, producing a response in a myotome associated with the innervated nerve.

The control unit 122 includes a touch screen display 140 and a base 142, which collectively contain the essential processing capabilities (software and/or hardware) for controlling the monitoring system 120. The control unit 122 may include an audio unit 118 that emits sounds according to a location of a surgical element with respect to a nerve. The patient module 124 is connected to the control unit 122 via a data cable 144, which establishes the electrical connections and communications (digital and/or analog) between the control unit 122 and patient module 124. The main functions of the control unit 122 include receiving user commands via the touch screen display 140, activating stimulation electrodes on the surgical access instruments, processing signal data according to defined algorithms, displaying received parameters and processed data, and monitoring system status and report fault conditions. The touch screen display 140 is preferably equipped with a graphical user interface (GUI) capable of communicating information to the user and receiving instructions from the user. The display 140 and/or base 142 may contain patient module interface circuitry (hardware and/or software) that commands the stimulation sources, receives digitized signals and other information from the patient module 124, processes the EMG responses to extract characteristic information for each muscle group, and displays the processed data to the operator via the display 140.

In one embodiment, the monitoring system 120 is capable of determining nerve direction relative to one or more of the surgical access instruments before, during and/or following the creation of an operative corridor to a surgical target site. Monitoring system 120 accomplishes this by having the control unit 122 and patient module 124 cooperate to send electrical stimulation signals to one or more of the stimulation electrodes provided on these instruments. Depending upon the location of the surgical access system 10 within a patient (and more particularly, to any neural structures), the stimulation signals may cause nerves adjacent to or in the general proximity of the surgical access system 10 to depolarize. This causes muscle groups to innervate and generate EMG responses, which can be sensed via the EMG harness 126. The nerve direction feature of the system 120 is based on assessing the evoked response of the various muscle myotomes monitored by the system 120 via the EMG harness 126.

By monitoring the myotomes associated with the nerves (via the EMG harness 126 and recording electrode 127) and assessing the resulting EMG responses (via the control unit 122), the surgical access system 10 is capable of detecting the presence of (and optionally the distant and/or direction to) such nerves. This provides the ability to actively negotiate around or past such nerves to safely and reproducibly form the operative corridor to a particular surgical target site, as well as monitor to ensure that no neural structures migrate into contact with the surgical access system 10 after the operative corridor has been established. In spinal surgery, for example, this is particularly advantageous in that the surgical access system 10 may be particularly suited for establishing an operative corridor to an intervertebral target site in a postero-lateral, trans-psoas fashion so as to avoid the bony posterior elements of the spinal column.

Figure 25:
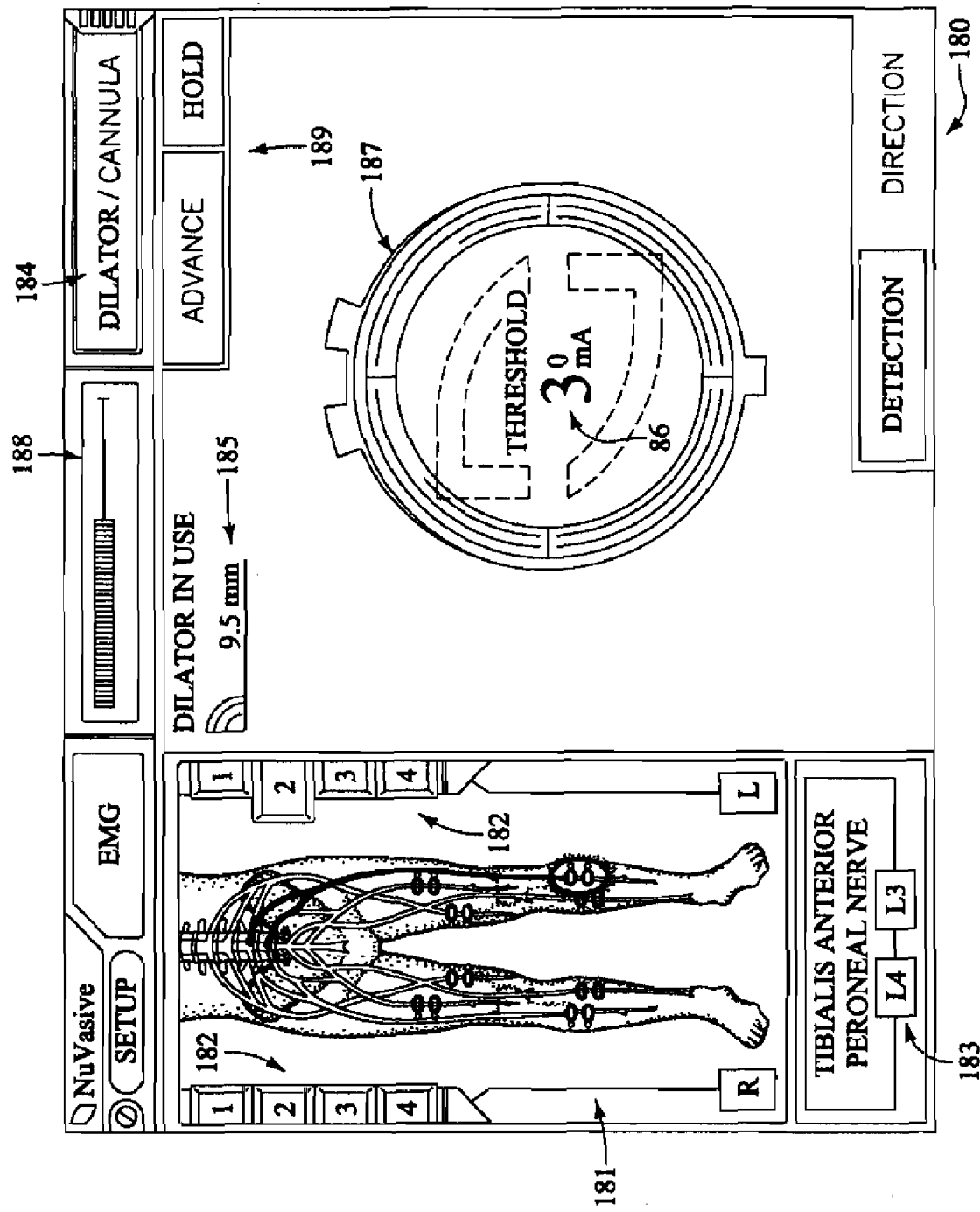
FIGS. 25-26 are screen displays illustrating exemplary features and information communicated to a user during the use of the nerve monitoring system of FIG. 23.
Figure 26:
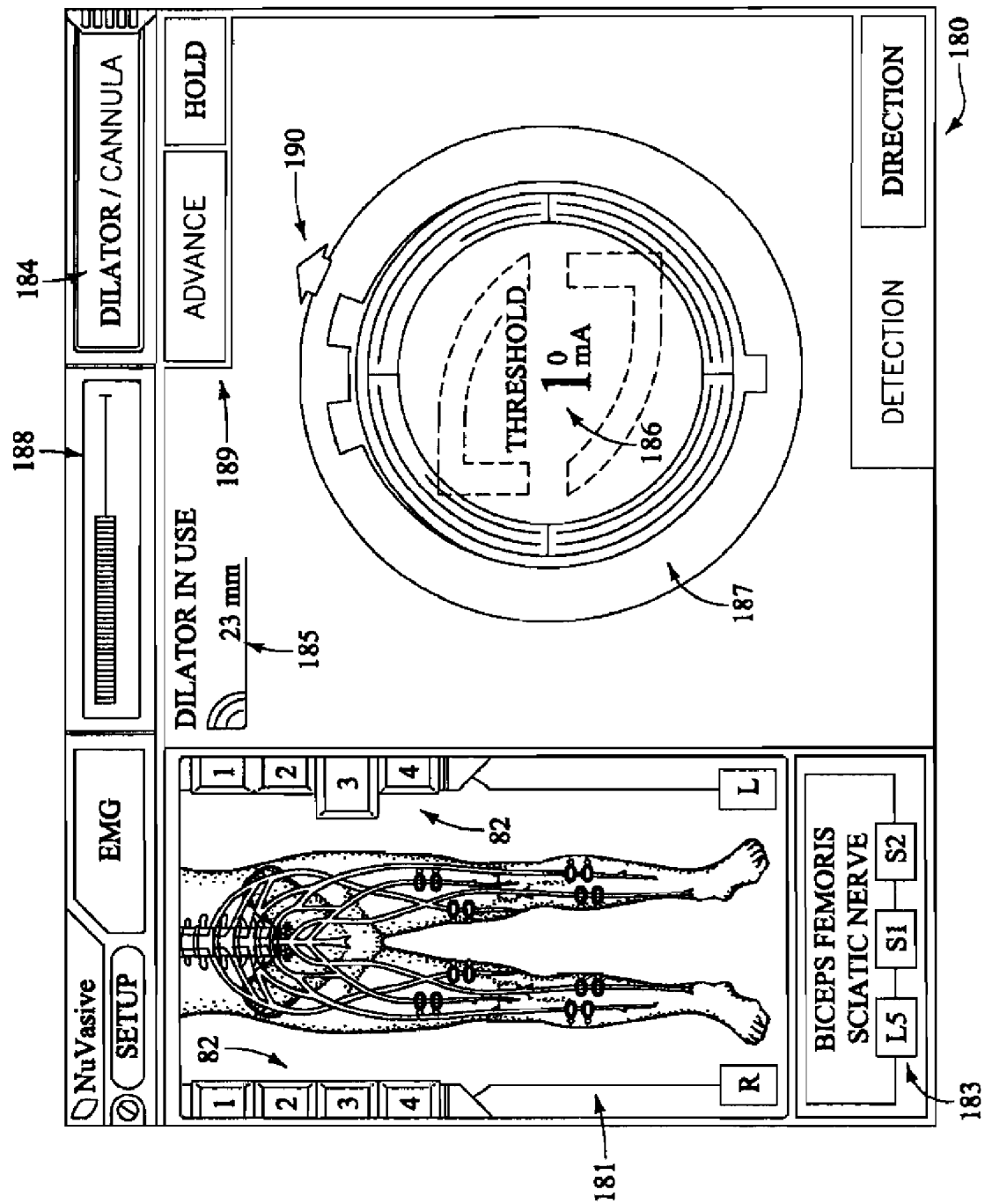

FIGS. 25-26 are exemplary screen displays (to be shown on the display 140) illustrating one embodiment of the nerve direction feature of the monitoring system shown and described with reference to FIGS. 23-24. These screen displays are intended to communicate a variety of information to the surgeon in an easy-to-interpret fashion. This information may include, but is not necessarily limited to, a display of the function 180 (in this case "DIRECTION"), a graphical representation of a patient 181, the myotome levels being monitored 182, the nerve or group associated with a displayed myotome 183, the name of the instrument being used 184 (in this case, a dilator 46, 48), the size of the instrument being used 185, the stimulation threshold current 186, a graphical representation of the instrument being used 187 (in this case, a cross-sectional view of a dilator 46, 48) to provide a reference point from which to illustrate relative direction of the instrument to the nerve, the stimulation current being applied to the stimulation electrodes 188, instructions for the user 189 (in this case, "ADVANCE" and/or "HOLD"), and (in FIG. 15) an arrow 190 indicating the direction from the instrument to a nerve. This information may be communicated in any number of suitable fashions, including but not limited to the use of visual indicia (such as alpha-numeric characters, light-emitting elements, and/or graphics) and audio communications (such as a speaker element). Although shown with specific reference to a dilating cannula (such as at 184), it is to be readily appreciated that the present invention is deemed to include providing similar information on the display 140 during the use of any or all of the various instruments forming the surgical access system 10 of the present invention, including the distraction assemblies 40, 50, the retractor blades 12, 16, 18 and/or the shim members 22, 24.

The surgical access system 10 of the present invention may be sold or distributed to end users in any number of suitable kits or packages (sterile and/or non-sterile) containing some or all of the various components described herein.

As evident from the above discussion and drawings, the present invention accomplishes the goal of gaining access a surgical target site in a fashion less invasive than traditional "open" surgeries and, moreover, does so in a manner that provides the ability to access such a surgical target site regardless of the neural structures required to be passed through (or near) in order to establish an operative corridor to the surgical target site. The present invention furthermore provides the ability to perform neural monitoring in the tissue or regions adjacent the surgical target site during any procedures performed after the operative corridor has been established. The surgical access system of the present invention can be used in any of a wide variety of surgical or medical applications, above and beyond the spinal applications discussed herein. Such spinal applications may include any procedure wherein instruments, devices, implants and/or compounds are to be introduced into or adjacent the surgical target site, including but not limited to discectomy, fusion (including PLIF, ALIF, TLIF and any fusion effectuated via a lateral or far-lateral approach and involving, by way of example, the introduction of bone products (such as allograft or autograft) and/or devices having ceramic, metal and/or plastic construction (such as mesh) and/or compounds such as bone morphogenic protein), total disc replacement, etc. . . . ).

Moreover, the surgical access system of the present invention opens the possibility of accessing an increased number of surgical target sites in a "less invasive" fashion by eliminating or greatly reducing the threat of contacting nerves or neural structures while establishing an operative corridor through or near tissues containing such nerves or neural structures. In so doing, the surgical access system of the present invention represents a significant advancement capable of improving patient care (via reduced pain due to "less-invasive" access and reduced or eliminated risk of neural contact before, during, and after the establishment of the operative corridor) and lowering health care costs (via reduced hospitalization based on "less-invasive" access and increased number of suitable surgical target sites based on neural monitoring). Collectively, these translate into major improvements to the overall standard of care available to the patient population, both domestically and overseas.

While certain embodiments have been described, it will be appreciated by those skilled in the art that variations may be accomplished in view of these teachings without deviating from the spirit or scope of the present application. For example, with regard to the monitoring system 120, it may be implemented using any combination of computer programming software, firmware or hardware. As a preparatory act to practicing the system 120 or constructing an apparatus according to the application, the computer programming code (whether software or firmware) according to the application will typically be stored in one or more machine readable storage mediums such as fixed (hard) drives, diskettes, optical disks, magnetic tape, semiconductor memories such as ROMs, PROMs, etc., thereby making an article of manufacture in accordance with the application. The article of manufacture containing the computer programming code may be used by either executing the code directly from the storage device, by copying the code from the storage device into another storage device such as a hard disk, RAM, etc. or by transmitting the code on a network for remote execution. As can be envisioned by one of skill in the art, many different combinations of the above may be used and accordingly the present application is not limited by the scope of the appended claims.

The invention claimed is:

1. A system for accessing a surgical target site, comprising:
a dilator system comprising a plurality of sequential dilators deliverable along a lateral, trans-psoas path to a targeted spinal site to create a distraction corridor;
a handle assembly including a first pivotable arm member, a second pivotable arm member that pivots relative to said first arm member in response to manual adjustment of a component of the handle assembly, and a translating member adapted to move longitudinally relative to said first and second arm members;
a first retractor blade having a generally concave inner-facing surface and being rigidly coupled to said first pivotable arm member prior to introduction toward the targeted spinal site, a second retractor blade having a generally concave inner-facing surface and being rigidly coupled to said second pivotable arm member prior to introduction toward the targeted spinal site, and a third retractor blade rigidly coupled to said translating member prior to introduction toward the targeted spinal site;
an intradiscal shim element that releasably mounts to the third retractor blade such that a maximum length of the intradiscal shim element extends generally parallel to a maximum length of the third retractor blade and a distal tip portion of the intradiscal shim element extends distally of the distal end of the third retractor blade, wherein the intradiscal shim element engages with a groove defined by the third retractor blade to penetrate into a spinal disc at the targeted spinal site when the intradiscal shim element is releasably mounted to the third retractor blade; and
said handle assembly being configured to simultaneously introduce said first, second and third retractor blades along the lateral, trans-psoas path toward the targeted spinal site in a closed position while the generally concave inner-facing surfaces of said first and second retractor blades engage with an outermost dilator of the dilator system and thereafter opened by pivoting said first and second pivotable arm members relative to one another to create an operative corridor to said surgical target site.

2. The system of claim 1, further comprising a K-wire configured to be advance along the lateral, trans-psoas path to the targeted spinal site and engage an annulus of said spinal disc, the K-wire further configured to extend entirely through a dilator of said dilator system from the annulus of the spinal disc to a position beyond a proximal most end of the dilator system.

3. The system of claim 2, wherein said K-wire has a first stimulation electrode at a distal tip of the K-wire.

4. The system of claim 1, wherein the intradiscal shim element includes an extension of sufficient height to distract vertebral bodies adjacent to said spinal disc at the targeted spinal site when the intradiscal shim element is releasably mounted to the third retractor blade.

5. The system of claim 1, further comprising at least one retractor extender capable of being detachably engaged with at least one of said first and second retractor blades to prevent the ingress of adjacent tissue into said operative corridor after said first, second and third retractor blades have been opened.

6. The system of claim 1, wherein at least one of said plurality of sequential dilators is equipped with at least one stimulation electrode.

7. The system of claim 6, further comprising a control unit capable of electrically stimulating said at least one stimulation electrode, sensing a response of a nerve depolarized by said stimulation, determining at least one of proximity and direction between said at least one stimulation electrode and said depolarized nerve based upon the sensed response, and communicating said at least one of proximity and direction to a user.

8. The system of claim 7, further comprising an electrode configured to sense a neuromuscular response of a muscle coupled to said depolarized nerve, the electrode being operable to send the response to the control unit.

9. The system of claim 8, wherein the control unit extracts characteristic information from the response detected by said electrode to determine at least one of proximity and direction between said at least one stimulation electrode and said depolarized nerve.

10. The system of claim 9, wherein the characteristic information includes a stimulation current threshold and said control unit displays the value of said stimulation current threshold.

11. The system of claim 7, further comprising at least one button for initiating the electrical stimulation from said control unit to said at least one stimulation electrode.

12. The system of claim 7, wherein the control unit comprises a display operable to display at least one of an electromyographic (EMG) response of said muscle coupled to said depolarized nerve and a stimulation threshold of said depolarized nerve.

13. The system of claim 7, wherein the control unit comprises a touch-screen display operable to receive commands from a user.

14. The system of claim 7, wherein at least one of said first, second and third retractor blades includes a stimulation electrode positioned near a distal end of said at least one of said first, second and third retractor blades.

15. The system of claim 1, wherein each of the plurality of sequential dilators includes a stimulation electrode at a distal region.

16. The system of claim 15, further comprising a K-wire configured to be advanced to the targeted spinal site and to engage an annulus of said spinal disc at the targeted spinal site, wherein at least one of the plurality of sequential dilators are deliverable over the K-wire.

17. The system of claim 1, wherein the first retractor blade includes a groove formed along said generally concave inner-facing surface of the first retractor blade.

18. The system of claim 17, further comprising a first retractor extender element that releasably mounts to the groove of the first retractor blade such that a maximum length of the first retractor extender element extends generally parallel to a maximum length of the first retractor blade and a distal tip portion of the first retractor extender element extends distally of the distal end of the first retractor blade when the first retractor extender element is releasably mounted to the first retractor blade.

19. The system of claim 1, wherein the third retractor blade includes a generally concave inner-facing surface and the groove of the third retractor blade is formed along the generally concave inner-facing surface.

20. The system of claim 19, wherein the intradiscal shim element includes at least one dovetail element to mate with the groove of the third retractor blade.

21. The system of claim 1, wherein the second retractor blade includes a groove formed along said generally concave inner-facing surface of the second retractor blade.

22. The system of claim 21, further comprising a second retractor extender element that releasably mounts to the groove of the second retractor blade such that a maximum length of the second retractor extender element extends generally parallel to a maximum length of the second retractor blade and a distal tip portion of the second retractor extender element extends distally of the distal end of the second retractor blade when the second retractor extender element is releasably mounted to the second retractor blade.

23. The system of claim 1, wherein said handle is configured to simultaneously move said first arm member and said second arm member.

24. The system of claim 1, wherein the first and second retractor blades simultaneously move when the handle assembly moves the first, second, and third retractor blades to the open position.

25. The system of claim 1, wherein said handle is configured to simultaneously move the first, second, and third retractor blades.

26. The system of claim 1, further comprising a shim insertion tool that releasably attaches to the intradiscal shim element during introduction of the intradiscal shim element toward the targeted spinal site.

27. The system of claim 1, further comprising a fiber optic cable for positioning within a wall of said first or second retractor blade to emit light toward the targeted spinal site.

28. The system of claim 1, wherein the handle assembly further includes a locking mechanism to selectively lock at least the first arm member in a retracted position such that the first retractor blade is spaced apart from the second retractor blade.

29. The system of claim 1, wherein the first, second, and third retractor blades define an operative corridor to the targeted spinal site when moved to the opened position such that an implant is deliverable through the operative corridor to the targeted spinal site.

30. A surgical retractor system for accessing a surgical target site, comprising:
a handle assembly including first and second pivotable arm members and a translating member adapted to move longitudinally relative to said first and second arm members;
a first retractor blade coupled to said first arm member prior to introduction to a targeted spinal site and having a length sufficient to extend laterally to the targeted spinal site, a second retractor blade coupled to said second arm member prior to introduction to the targeted spinal site and having a length sufficient to extend laterally to the targeted spinal site, and a third retractor blade coupled to said translating member prior to introduction to the targeted spinal site and having a length sufficient to extend laterally to the targeted spinal site, said first, second, and third retractor blades defining a corridor extending from a proximal end of each retractor blade to a distal end of each retractor blade and between said retractor blades;
an intradiscal shim element that releasably mounts to a groove formed in the third retractor blade such that a distal tip portion of the intradiscal shim element extends distally of the distal end of the third retractor blade and penetrates into a spinal disc at the targeted spinal site when the intradiscal shim element is releasably mounted to the third retractor blade;
a first retractor extender element that releasably mounts to the first retractor blade such that a maximum length of the first retractor extender element extends generally parallel to a maximum length of the first retractor blade and a distal tip portion of the first retractor extender element extends distally of the distal end of the first retractor blade when the first retractor extender element is releasably mounted to the first retractor blade; and
said handle assembly being operable to pivot said first arm member and said second arm member and translate said translating member in a linear path relative said first and second arm members, thereby increasing the size of the corridor between said retractor blades to provide access to the targeted spinal site.

31. The surgical retractor system of claim 30, wherein said first retractor blade includes a pair of grooves for engagement with said first retractor extender element.

32. The surgical retractor system of claim 31, wherein at least one of said grooves is a dove-tail groove.

33. The surgical retractor system of claim 31, wherein at least a portion of said first retractor extender element slides down said first retractor blade within said pair of grooves.

34. The surgical retractor system of claim 30, wherein said intradiscal shim element includes an extension of sufficient height to distract vertebral bodies adjacent to said spinal disc at the targeted spinal site when the intradiscal shim element is releasably mounted to the third retractor blade.

35. The surgical retractor system of claim 34, wherein said intradiscal shim element fixes the position of said third blade relative to said targeted spinal site when said extension is adapted to penetrate into said spinal disc.

36. The surgical retractor system of claim 35, wherein said handle assembly and first, second, and third retractor blades are configured such that said third retractor blade can be fixed prior to enlarging said corridor and said first and second retractor blades move relative to said third retractor blade.

37. The surgical system of claim 30, wherein said distal tip portion of said first retractor extender element includes a generally horizontal extension extending away from said corridor when said first retractor extender element is engaged with said first retractor blade.

38. The surgical retractor system of claim 30, further comprising at least one dilator advanceable to said targeted spinal site prior to said retractor blades and dimensioned to slidably receive said retractor blades thereabout to guide said retractor blades to said targeted spinal site.

39. The surgical retractor system of claim 38, wherein at least one of said dilator, first retractor blade, second retractor blade, and third retractor blade are equipped with at least one stimulation electrode.

40. The surgical retractor system of claim 30, wherein at least one of said first retractor blade, second retractor blade, and third retractor blade, is equipped to direct light to said targeted spinal site.

41. The surgical retractor system of claim 40, wherein at least one light cable extends along at least a portion of the length of at least one of said first retractor blade, second retractor blade, and third retractor blade.

42. The surgical retractor system of claim 30, further comprising a dilator system comprising a plurality of sequential dilators deliverable along a lateral, trans-psoas path to the targeted spinal site to create a distraction corridor, wherein said handle is configured to simultaneously introduce said first, second and third retractor blades along the lateral, trans-psoas path toward the targeted spinal site in a closed position while the first, second, and third retractor blades slidably engage with an outermost dilator of the dilator system.

43. The surgical retractor system of claim 42, wherein each of the plurality of sequential dilators includes a stimulation electrode at a distal region.

44. The surgical retractor system of claim 43, further comprising a K-wire dimensioned to extend through said plurality of sequential dilators and configured to be advanced to the targeted spinal site and to engage an annulus of said spinal disc at the targeted spinal site.

45. The surgical retractor system of claim 30, wherein the first retractor blade is rigidly coupled to said first arm member prior to introduction to the targeted spinal site, the second retractor blade is rigidly coupled to said second arm member prior to introduction to the targeted spinal site, and the third retractor blade is rigidly coupled to said translating member prior to introduction to the targeted spinal site.

46. The surgical retractor system of claim 30, wherein the first retractor blade includes a generally concave inner-facing surface and a groove formed along the generally concave inner-facing surface.

47. The surgical retractor system of claim 46, wherein the first retractor extender element releasably mounts to the groove formed along the generally concave inner-facing surface of the of the first retractor blade groove.

48. The surgical retractor system of claim 30, wherein the third retractor blade includes a generally concave inner-facing surface and the groove of the third retractor blade is formed along the generally concave inner-facing surface.

49. The surgical retractor system of claim 48, wherein the intradiscal shim element includes at least one dovetail element to mate with the groove of the third retractor blade.

50. The surgical retractor system of claim 30, wherein the second retractor blade includes a generally concave inner-facing surface and a groove formed along the generally concave inner-facing surface.

51. The surgical retractor system of claim 50, further comprising a second retractor extender element that releasably mounts to the groove of the second retractor blade such that a maximum length of the second retractor extender element extends generally parallel to a maximum length of the second retractor blade and a distal tip portion of the second retractor extender element extends distally of the distal end of the second retractor blade when the second retractor extender element is releasably mounted to the second retractor blade.

52. The surgical retractor system of claim 30, wherein said handle is operable to simultaneously move said first arm member and said second arm member.

53. The surgical retractor system of claim 30, wherein said handle is operable to simultaneously move said first, second, and third retractor blades.

54. The surgical retractor system of claim 30, further comprising a shim insertion tool that releasably attaches to the intradiscal shim element during introduction of the intradiscal shim element toward the targeted spinal site.

55. The surgical retractor system of claim 30, further comprising a fiber optic cable for positioning within a wall of said first or second retractor blade to emit light toward the targeted spinal site.

56. The surgical retractor system of claim 30, wherein the handle assembly further includes a locking mechanism to selectively lock at least the first arm member in a retracted position such that the first retractor blade is spaced apart from the second retractor blade.

57. The surgical retractor system of claim 30, wherein the handle assembly is operable to move said first arm member and said second arm member thereby increasing the size of the corridor between said first, second, and third retractor blades such that an implant is deliverable through the corridor to the targeted spinal site.

* * * * *

(12) INTER PARTES REEXAMINATION CERTIFICATE (1179th)
United States Patent
Miles et al.

(10) Number: US 7,819,801 C1
(45) Certificate Issued: Sep. 23, 2015

(54) SURGICAL ACCESS SYSTEM AND RELATED METHODS

(75) Inventors: Patrick Miles, San Diego, CA (US); Scot Martinelli, Poway, CA (US); Eric Finley, Lancaster, CA (US); James Gharib, San Diego, CA (US); Allen Farquhar, San Diego, CA (US); Norbert Kaula, Arvada, CO (US); Jeffrey Blewett, San Diego, CA (US); Goretti Medeiros, legal representative, Plantsville, CT (US)

(73) Assignee: NUVASIVE, INC., San Diego, CA (US)

Reexamination Request:
No. 95/001,889, Feb. 9, 2012

Reexamination Certificate for:
Patent No.: 7,819,801
Issued: Oct. 26, 2010
Appl. No.: 10/789,797
Filed: Feb. 27, 2004

Related U.S. Application Data

(60) Provisional application No. 60/450,806, filed on Feb. 27, 2003.

(51) Int. Cl.
*A61B 1/32* (2006.01)
*A61B 17/02* (2006.01)

(52) U.S. Cl.
CPC .. *A61B 1/32* (2013.01); *A61B 17/02* (2013.01)

(58) Field of Classification Search
None
See application file for complete search history.

(56) References Cited

To view the complete listing of prior art documents cited during the proceeding for Reexamination Control Number 95/001,889, please refer to the USPTO's public Patent Application Information Retrieval (PAIR) system under the Display References tab.

*Primary Examiner* — Beverly M Flanagan

(57) ABSTRACT

A surgical access system including a tissue distraction assembly and a tissue retraction assembly, both of which may be equipped with one or more electrodes for use in detecting the existence of (and optionally the distance and/or direction to) neural structure before, during, and after the establishment of an operative corridor to a surgical target site.

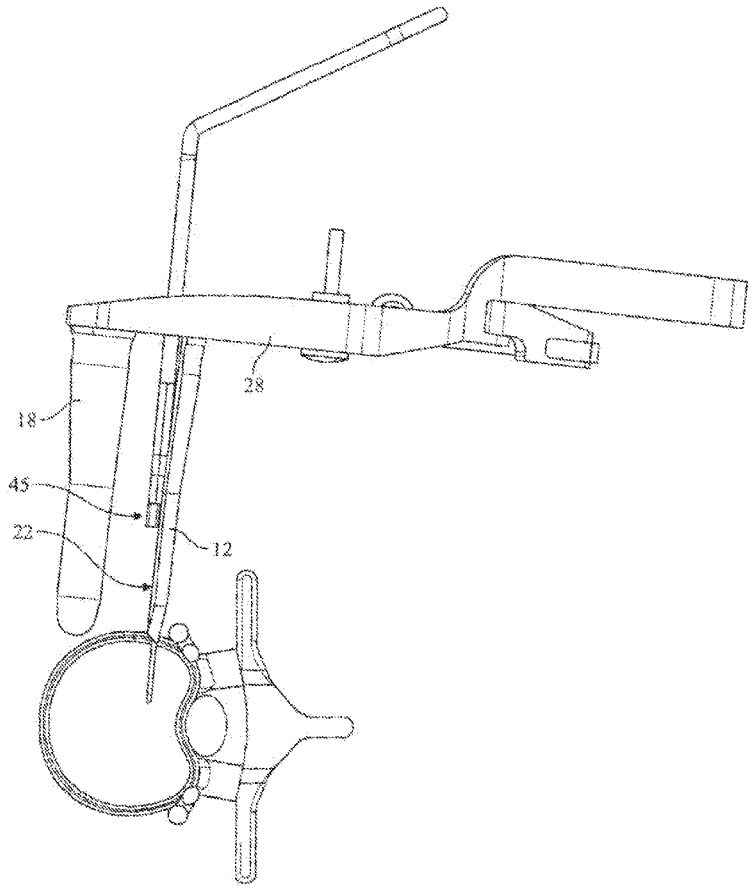

INTER PARTES REEXAMINATION CERTIFICATE

NO AMENDMENTS HAVE BEEN MADE TO THE PATENT

AS A RESULT OF REEXAMINATION, IT HAS BEEN DETERMINED THAT:

The patentability of claims 1, 2, 6-10, 12-17, 19, 21, 26, 27 and 29 is confirmed.

Claims 3-5, 11, 18, 20, 22-25, 28 and 30-57 were not reexamined.

\* \* \* \* \*